United States Patent [19]

Noguchi et al.

[11] 4,224,225

[45] Sep. 23, 1980

[54] 2-ARYLNAPHTHO[1,8-bc]FURAN-5-ONES

[75] Inventors: Yasuhiro Noguchi; Syunichi Kondo; Akihiro Matsufuji; Hisatake Ono, all of Asaka; Toshio Uchida, Shizuoka, all of Japan

[73] Assignee: Fuji Photo Film Co., Ltd., Minami-ashigara, Japan

[21] Appl. No.: 953,318

[22] Filed: Oct. 20, 1978

[30] Foreign Application Priority Data

Oct. 20, 1977 [JP] Japan .............................. 52-126270

[51] Int. Cl.² .......................................... C07D 307/92
[52] U.S. Cl. ............................ 260/346.71; 430/281; 430/343; 430/916; 430/919
[58] Field of Search ................................... 260/346.71

[56] References Cited
PUBLICATIONS

Barton et. al., J. Chem. Soc. (C), 1971, pp. 2193–2203.

*Primary Examiner*—Henry R. Jiles
*Assistant Examiner*—Bernard Dentz
*Attorney, Agent, or Firm*—Sughrue, Rothwell, Mion, Zinn and Macpeak

[57] ABSTRACT

2-Arylnaphtho[1,8-bc]furan-5-ones represented by general formula (I):

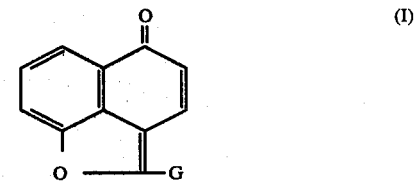

wherein G represents a substituted phenyl group, an unsubstituted or substituted 1-naphthyl group and an unsubstituted or substituted 2-naphthyl group, with the substituents being selected from the group consisting of a straight chain or branched chain alkyl group having 1 to 5 carbon atoms, a straight chain or branched chain alkoxy group having 1 to 3 carbon atoms and a halogen atom; are disclosed as well as photopolymerizable compositions containing at least one of the above compounds as a photopolymerization initiator for addition polymerizable ethylenically unsaturated compounds.

4 Claims, No Drawings

2-ARYLNAPHTHO[1,8-bc]FURAN-5-ONES

BACKGROUND OF THE INVENTION

1. Field of the Invention

The invention relates to novel compounds, 2-arylnaphtho[1,8-bc]furan-5-ones (hereinafter, referred to as naphthofuranones) and photopolymerizable compositions containing naphthofuranones as a photopolymerization initiators for addition polymerizable ethylenically unsaturated compounds.

2. Description of the Prior Art

It is well known that when an unsaturated compound which can be hardened upon irradiation is used as the polymerizable component of a composition such as paint, a printing ink, an adhesive, etc., and such a composition is subject to the action of electromagnetic waves such as visible rays, ultraviolet rays, X-rays, etc., or particle rays such as electron rays, neutron rays, alpha rays, etc., the aforesaid component is hardened by polymerization and further when the composition is subjected to radiation in the presence of a photopolymerization initiator, the polymerization rate of the composition increases remarkably. These techniques are described in, for example, U.S. Pat. Nos. 3,551,235, 3,551,246, 3,551,311 and 3,558,387, Belgian Pat. No. 808,179 and Japanese Patent Application (OPI) No. 110,781/1974 (The term "OPI" as used herein refers to a "published unexamined Japanese patent application") (corresponding to U.S. patent application Ser. No. 328,442, filed Jan. 31, 1973) and now abandoned.

The hardened products obtained by such techniques possess such advantages as excellent flexibility, chemical resistance, abrasion resistance, luster, adhesive property but, on the other hand, they also possess such disadvantages as a low sensitivity, which means they require a long period of time for image exposure for the formation of images utilizing the composition. Therefore, problems arise such as in the case of delicate image exposure, images having good image quality cannot be reproduced if even the slightest vibration occurs in the operation. Furthermore, the irradiation energy of the light source or the particle ray source must be increased for exposure, which results in the deformation and deterioration of the layer of the composition by the large amount of heat which accompanies the increased irradiation energy. Also, compositions containing the aforesaid conventional hardenable ethylenically unsaturated compounds have the disadvantage that when the composition is provided with a comparatively high hardening response or sensitivity, the composition tends to harden during storage due to heat.

SUMMARY OF THE INVENTION

The inventors have made various extensive investigations of photosensitive compositions having excellent hardening response with respect to improving the photopolymerization initiator incorporated in the compositions and as the result thereof they have found that specific naphthofuranones are excellent photopolymerization initiators which greatly increase the rate of photopolymerization of ethylenically unsaturated compounds and show none or very few of the disadvantages discussed above which are encountered using conventional photopolymerization initiators.

A first object of this invention is to provide 2-arylnaphtho[1,8-bc]furan-5-ones represented by general formula (I) described later.

A second object of this invention is to provide a photopolymerizable composition containing, as essential components, (a) at least one ethylenically unsaturated addition polymerizable compound and (b) at least one of the abovedescribed 2-arylnaphtho[1,8-bc]furan-5-ones as a photopolymerization initiator.

A third object of this invention is to provide a highly sensitive photopolymerizable composition containing, as the essential components, (a) at least one ethylenically unsaturated compound and a photopolymerization initiator which is a combination of (b) at least one of the 2-arylnaphtho[1,8-bc]furan-5-ones and (c) at least one of the nitrogen compounds represented by general formulae (III) to (XII) disclosed below.

The fourth object of this invention is to provide a process of producing the above-described photopolymerization initiators in one reaction vessel without using any raw materials which present a danger to occupational safety and wherein the products are easily isolated and purified.

The fifth object of this invention is to provide a photopolymerizable composition having excellent heat stability and capable of providing products having long shelf life.

The sixth object of this invention is to provide a naphthofuranone capable of giving a photo print out composition together with an oxidizable leuco dye which is colored by the action of a photo-oxidative photo initiator.

These and other objects are attained by the present invention, wherein:

A primary embodiment of this invention is a 2-arylnaphtho[1,8-bc]furan-5-ones represented by general formula (I):

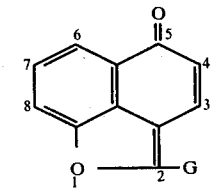

(I)

wherein G represents a substituted phenyl group, an unsubstituted or substituted 1-naphthyl group and an unsubstituted or substituted 2-naphthyl group, with the substituents being selected from the group consisting of a straight chain or branched chain alkyl group having 1 to 5 carbon atoms, a straight chain or branched chain alkoxy group having 1 to 3 carbon atoms and a halogen atom.

A subgeneric embodiment of this invention is a 2-arylnaphtho[1,8-bc]furan-5-ones of the above-described general formula (I) wherein G is a phenyl group substituted with one or two of a methyl group, an ethyl group, an n-propyl group, an n-butyl group, an isopropyl group, an isobutyl group, a sec-butyl group, a tert-butyl group, a methoxy group, an ethoxy group, a bromine atom or a chlorine atom; or a 1-naphthyl group or a 2-naphthyl group.

A third embodiment of this invention is a photopolymerizable composition containing, as the essential components, (a) at least one ethylenically unsaturated addition polymerizable compound and (b) at least one photopolymerization initiator, wherein the photopolymerization initiator is a 2-arylnaphtho[1,8-bc]furan-5-one represented by general formula (II):

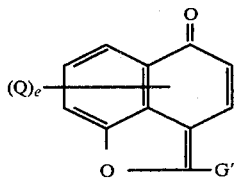
(II)

wherein G' represents an unsubstituted or substituted phenyl group, an unsubstituted or substituted 1-naphthyl group and an unsubstituted or substituted 2-naphthyl group, with one or more substituents selected from the group consisting of a straight chain or branched chain alkyl group having 1 to 5 carbon atoms, a straight chain or branched chain alkoxy group having 1 to 5 carbon atoms, a halogen atom, a hydroxy group, a cyano group, a phenyl group, a benzoyl group, a carboxylic acid amido group having 1 to 3 carbon atoms and a mono- or dialkyl-substituted amino group having 1 to 3 carbon atoms; Q represents a halogen atom, an unsubstituted or substituted lower alkyl group having 1 to 5 carbon atoms and an N-alkyl-substituted aminoalkyl group; e is an integer of 1 to 5; when e is an integer of 2 or more, Q may be the same or different.

A further embodiment of this invention is a photopolymerizable composition as described above, wherein said composition further contains (c) at least one nitrogen-containing compound represented by any one of the following general formulae (III) to (XII) as the photopolymerization initiator:

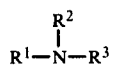
(III)

wherein $R^1$, $R^2$ and $R^3$ each represents an alkyl group, an aryl group, an aralkyl group, or a substituted alkyl group; said $R^1$, $R^2$ and $R^3$ may be the same or different.

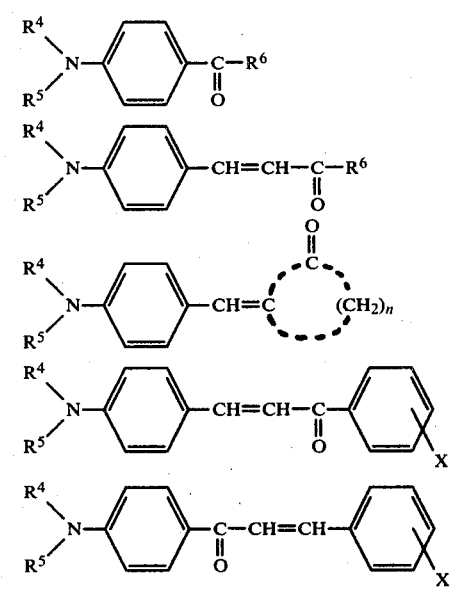

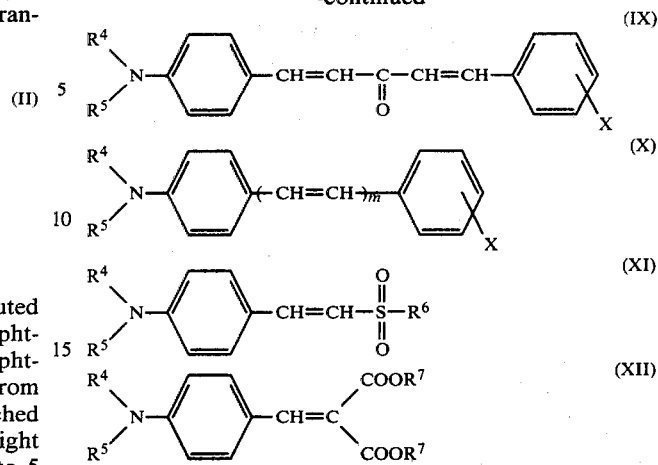

In formulae (IV) to (XII), $R^4$ and $R^5$, which may be the same or different, each represents an alkyl group or a substituted alkyl group; $R^6$ represents an alkyl group, an aryl group, an aralkyl group, a substituted alkyl group, an alkoxy group, an aryloxy group, or a monovalent residue of a 5-membered or 6-membered heteroaromatic ring containing a nitrogen atom, a sulfur atom, or an oxygen atom; $R^7$ represents an alkyl group, an aryl group, or an aralkyl group; m represents 1 or 2; n represents a positive integer of 3 to 8; and X represents a substituent wherein the value, i.e., the Hammett's substituent constant, is in a range of from about −0.9 to about +0.7. Compounds of the formula (III) are described in Japanese Patent Application (OPI) No. 110,781/1974 (corresponding to U.S. patent application Ser. No. 328,442, filed Jan. 31, 1973) and U.S. Pat. No. 3,945,833 and Compounds of the formula (IV) are described in Japanese Patent Application (OPI) No. 50,440/1975. Compounds of the formulae (V) to (XII) are described in Japanese Patent Application (OPI) Nos. 65,381/1978 and 90,387/1978 (corresponding to U.S. patent application Ser. No. 870,692, filed Jan. 19, 1978) and Japanese Patent Application Nos. 22,983/1977 and 24,631/1977.

Another embodiment of this invention is a photosensitive composition comprising a 2-arylnaphtho[1,8-bc]furan-5-one represented by the general formula (II) set forth above and an oxidizable leuco dye.

Still another embodiment of this invention is a photopolymerizable photosensitive material having on a support a layer of a photopolymerizable composition containing (a) at least one ethylenically unsaturated addition polymerizable compound and (b) at least one photopolymerization initiator, wherein said photopolymerization initiator is a 2-arylnaphtho[1,8-bc]furan-5-one represented by general formula (II) set forth above.

DETAILED DESCRIPTION OF THE INVENTION

Throughout this specification, two arylnaphthofuranone formulae (I) and (II) are presented. Formula (I) is presented for the purpose of claiming the compound per se and as such it does not include the prior art compound when G is an unsubstituted phenyl discussed below. Formula (II), on the other hand, is presented for the purpose of claiming photopolymerizable and photosensitive compositions and products. Since the prior art does not recognize the use of the compounds for this purpose as later pointed out, formula (II) includes those compounds where G' is an unsubstituted phenyl group.

In the novel compounds represented by general formula (I) (the numerals of 1 to 8 added to the chemical structural formula are position numbers), G represents a substituted phenyl group, an unsubstituted or substituted 1-naphthyl group and an unsubstituted or substituted 2-naphthyl group, with the substituents being selected from the group consisting of a straight chain or branched chain alkyl group having 1 to 5 carbon atoms, a straight chain or branched chain alkoxy group having 1 to 3 carbon atoms and a halogen atom.

Preferred examples of the above-described compounds are compounds wherein G is a phenyl group substituted with one or two of a methyl group, an ethyl group, a propyl group, a butyl group, an isopropyl group, an isobutyl group, a secbutyl group, a tert-butyl group, a methoxy group, an ethoxy group, a chlorine atom or a bromine atom; or a 1-naphthyl group or a 2-naphthyl group.

As is clear by comparing general formula (I) with general formula (II), the compounds of general formula (II) correspond to the compounds of general formula (I) except in general formula (II) G' can be an unsubstituted phenyl group. Separate formulae are presented for the purpose of claiming the compound and the photopolymerizable or photosensitive composition as pointed out above.

The compounds of general formula (II) can be prepared in the manner described in S. R. Cooper, *Organic Synthesis*, Vol. 21, 103 (1941) or *J. Chem. Soc.* (C), 1971, 2166–2194. For example, the compound of general formula (II) can be synthesized in one reaction vessel by reacting 20 g of a 1,5-dihydroxynaphthalene with 30 g of an aromatic monocarboxylic acid such as benzoic acids, naphthoic acids, etc., under heating at 150° C. for 1 hour with adding 17 g of zinc chloride over 5 minute period without a solvent as shown in the following reaction formula:

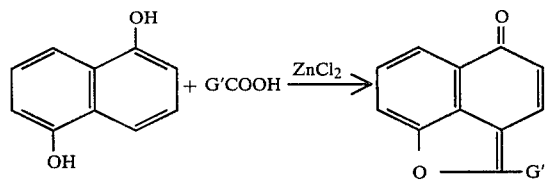

in the formula, G' represents an unsubstituted or substituted phenyl group, 1-naphthyl group or 2-naphthyl group.

The 1,5-dihydroxynaphthalenes (1,5-naphthalenediols) used in the above-described reaction may be unsubstituted or substituted but they cannot be substituted at both the 4- and 8-position in the following general formula (XIII):

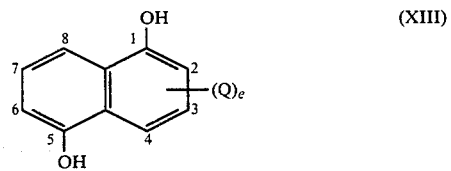

possible examples of the substituent Q are halogen (such as fluorine, chlorine, bromine, and iodine), a substituted or unsubstituted lower alkyl group of 1 to 5 carbon atoms (such as a methyl, ethyl, propyl, isopropyl, allyl, 2-methylpropenyl group, etc.), and an N-alkyl-substituted aminoalkyl group (examples of the alkyl group on the nitrogen atom are a straight chain or branched chain alkyl group having 1 to 5 carbon atoms and a cyclic alkyl group having 5 to 7 carbon atoms and examples of the alkyl group are methyl, ethyl, propyl groups); e is an integer of 1 to 5; when e is an integer of 2 or more, Q may be the same or different.

Suitable 1,5-naphthalenediols used in this invention are 1,5-naphthalenediol, 2,6-dibromo-1,5-naphthalenediol, 2,4-dichloro-1,5-naphthalenediol, 2,4-dibromo-1,5-naphthalenediol, 2,6-bis[(cyclohexylamino)methyl]-1,5-naphthalenediol, 2,6-bis[(propylamino)methyl]-1,5-naphthalenediol, 2,6-di-tert-butyl-1,5-naphthalenediol, 2,6-bis(2-methylpropenyl)-1,5-naphthalenediol, etc.

Also, typical examples of the compounds used as the aromatic monocarboxylic acids in this invention are unsubstituted benzoic acid, 1-naphthoic acid, and 2-naphthoic acid and the nuclear-substituted acids thereof.

Substituted benzoic acids used in making the compounds are represented by the following general formula (XIV):

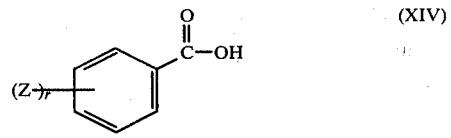

wherein Z represents a straight chain or branched chain alkyl group having 1 to 5 carbon atoms (such as methyl, ethyl, n-propyl, n-butyl, isopropyl, isobutyl, sec-butyl, tert-butyl groups, etc.), a straight chain or branched chain alkoxy group having 1 to 5 carbon atoms (such as methoxy, ethoxy, propoxy, isopropoxy groups, etc.), a halogen atom (such as fluorine, chlorine, bromine, iodine, etc.), a hydroxy group, a cyano group, a phenyl group, a benzoyl group, a carboxylic acid amido group having 1 to 3 carbon atoms, a mono- or dialkyl-substituted amino group having 1 to 3 carbon atoms, etc.; and r is an integer of 1 to 5; when r is an integer of 2 or more, the substituents Z may be the same or different.

Practical examples of the phenyl nucleus-substituted benzoic acid used are o-toluic acid, m-toluic acid, p-toluic acid, p-ethylbenzoic acid, p-isopropylbenzoic acid, p-butylbenzoic acid, p-tert-butylbenzoic acid, 3,4-dimethylbenzoic acid, 3,5-dimethylbenzoic acid, o-anisic acid, m-anisic acid, p-anisic acid, 2,4-dimethoxybenzoic acid, 3,4-dimethoxybenzoic acid (veratric acid), 2,3-dimethoxybenzoic acid (o-veratric acid), o-ethoxybenzoic acid, 3-methoxy-4-methylbenzoic acid, 1-ethoxybenzoic acid, p-propoxybenzoic acid, o-bromobenzoic acid, m-bromobenzoic acid, p-bromobenzoic acid, o-chlorobenzoic acid, m-chlorobenzoic acid, p-fluorobenzoic acid, 3,4-dichlorobenzoic acid, o-hydroxybenzoic acid, m-hydroxybenzoic acid, p-hydroxybenzoic acid, 4-hydroxy-3-methoxybenzoic acid, 2-biphenylcarboxylic acid, 4-biphenylcarboxylic acid, o-benzoylbenzoic acid, p-acetamidobenzoic acid, m-dimethylaminobenzoic acid, p-methylaminobenzoic acid, m-cyanobenzoic acid, and p-cyanobenzoic acid.

Furthermore, in the case of using nucleus-substituted naphthoic acid as the monocarboxylic acid, examples of the suitable nucleus substituents are halogen atoms (such as fluorine, chlorine, bromine, iodine, etc.), and a lower alkyl group having 1 to 3 carbon atoms, and the number of the substituents is preferably 1 or more. Moreover, the carboxylic acid anhydrides or carboxylic acid chlorides derived from the aforesaid benzoic acids or naphthoic acids can be used as the raw materials for the condensation.

Practical examples of the nucleus-substituted naphthoic acid are 2-chloro-1-naphthoic acid, 4-chloro-1-naphthoic acid, 5-chloro-1-naphthoic acid, 8-chloro-1-naphthoic acid, 4-fluoro-1-naphthoic acid, 4-bromo-1-naphthoic acid, 5-iodo-1-naphthoic acid, 5,8-dichloro-1-naphthoic acid, 1-chloro-2-naphthoic acid, 3-chloro-2-naphthoic acid, 5-chloro-2-naphthoic acid, 4,5-dichloro-2-naphthoic acid, 1-bromo-2-naphthoic acid, 2-methyl-1-naphthoic acid, 6-methyl-1-naphthoic acid, 8-methyl-2-naphthoic acid, etc.

In the simplest manner of reacting the above-described 1,5-naphthalenediol and aromatic monocarboxylic acid, the aromatic monocarboxylic acid is first fused at a temperature higher than the melting point thereof, while stirring, a zinc chloride powder and the 1,5-naphthalenediol are added successively to the fused monocarboxylic acid in this or the opposite order to carry out the reaction without using a reaction solvent. Usually, the reaction is carried out in the presence of 0.5 to 4 mols, preferably 1.2 to 2.5 mols of the aromatic monocarboxylic acid per mol of the 1,5-naphthalenediol and also 0.1 to 4 equivalent, preferably 0.4 to 2 equivalent of zinc chloride.

In carrying out the reaction in the above-described fused state, the reaction temperature is in a temperature range of more than 5° C. higher, preferably 10° to 30° C. higher, than the melting point of the aromatic monocarboxylic acid (however, when the temperature range does not reach 150° C., the temperature range is 150° to 170° C.) and in such case, the desired product can be produced in good yield with little side reaction. The progress of the reaction can be easily monitored by silica gel thin layer chromatography and the result can be used to determine the reaction time.

In the case of fusing and condensing the 1,5-naphthalenediol and the aromatic carboxylic acid, low reaction temperatures can be selected if the melting point of the aromatic carboxylic acid is low. In this case, the naphthofuranone can be obtained in a high yield. Such an aromatic carboxylic acid is crystalline having a melting point of lower than 220° C., preferably lower than 190° C. Furthermore, a benzoic acid derivative substituted with a substituent having a Hammett's substituent constant $\sigma$ in the range of about $-0.9$ to about $+0.5$ and containing no nitrogen atom tends to give higher yields for the naphthofuranone than other benzoic acid derivatives having substituents which do not meet the above-described requirements. (In this specification, the definition of the Hammett's $\sigma$ value is by J. E. Leffler (translated by Yuho Tsuno), *Theory of Organic Reaction Rate,* published by Hirokawa Shoten in 1968.) Furthermore, the naphthofuranone obtained from a carboxylic acid which does not have a hydroxyl group is easily separated from unreacted raw materials and side products by extraction with an aqueous sodium hydroxide solution as will be described later.

In conclusion, the claimed naphthofuranone can be produced in a high yield and can be isolated in a simple manner by reacting unsubstituted benzoic acid or naphthoic acid, or a benzoic acid derivative having a Hammett's substitution constant $\sigma$ within a range of about $-0.9$ to about $+0.5$, where the substituent does not contain a hydroxyl group or a nitrogen atom and has a melting point of lower than 190° C. at a temperature range of from about 120° C. to about 250° C., preferably from about 150° C. to about 180° C. or from about 150° C. to a temperature about 40° C. higher than the melting point of the substituted benzoic acid followed by separation in a manner which will be described later.

Examples of the carboxylic acid component of the naphthofuranone which can be produced in such a simple manner, i.e., by fusing the acid and the naphthalenediol, can be represented by the following general formula (XV):

wherein G" represents a phenyl group or a 1- or 2-naphthyl group; and $R^8$ and $R^9$ each represents a straight chain or branched chain lower alkyl group having 1 to 5 carbon atoms, a straight chain or branched chain alkoxy group having 1 to 3 carbon atoms, a halogen atom (such as fluorine, chlorine, bromine, and iodine), or a hydrogen atom, and $R^8$ and $R^9$ may be the same or different. Practical examples of the lower alkyl group are methyl group, ethyl group, n-propyl group, n-butyl group, isopropyl group, isobutyl group, sec-butyl group, and tert-butyl group and practical examples of the alkoxy group are methoxy group, ethoxy group, propoxy group, and isopropoxy group.

Suitable examples of carboxylic acids having the above general formula are benzoic acid, 1-naphthoic acid, 2-naphthoic acid, o-anisic acid, m-anisic acid, p-anisic acid, veratric acid, o-veratric acid, o-ethoxybenzoic acid, p-propyloxybenzoic acid, o-toluic acid, m-toluic acid, p-toluic acid, 3,5-dimethylbenzoic acid, p-ethylbenzoic acid, p-isopropylbenzoic acid, p-n-butylbenzoic acid, p-tert-butylbenzoic acid, 3-methoxy-4-methylbenzoic acid, o-bromobenzoic acid, m-bromobenzoic acid, o-chlorobenzoic acid, and m-chlorobenzoic acid.

When the carboxylic acid component has a melting point over 190° C., the reaction may be carried out in the fused state described above but it is preferred to use a reaction solvent (such as nitrobenzene, 1,1,2,2-tetrachloroethane, etc.) usually employed in a Friedel-Crafts reaction in the reaction. Furthermore, in place of zinc chloride, an acylating catalyst for Friedel-Crafts reaction, such as aluminum chloride, polyphosphoric acid, etc., may be used or such an acylating catalyst may be used in combination with zinc chloride.

The 2-arylnaphtho[1,8-bc]furan-5-one thus prepared can be isolated from the reaction mixture by any of the following techniques.

(1) recrystallization from hot alcohol or hexane, (2) the reaction mixture may be solidified, pulverized and extracted with an aqueous sodium hydroxide solution, and then the naphthofuranone can be extracted from the residue using benzene or toluene, and (3) the reaction mixture may be dissolved in benzene or toluene, washed with an aqueous sodium hydroxide solution, and concentrated in the organic layer.

The crude product thus-separated by either of the above-described methods can be treated with activated carbon, if necessary, and purified in any manner ordinarily used for the purification of solid materials, e.g., such as recrystallization, sublimation, etc. As a matter of course, the product can be purified further by using silica gel or alumina column chromatography.

The structure of the 2-arylnaphtho[1,8-bc]furan-5-ones produced in this invention can be verified by various analytical methods such as elementaly analysis, infrared absorption spectra (IR), mass spectra, NMR, etc.

Practical examples of the 2-arylnaphtho[1,8-bc]-furan-5-ones produced by the above processes are listed in Table 1 and detailed processes of producing them and their various analytical values are reported in the synthesis examples shown later.

TABLE 1

| Compound No. | Name of Compound |
| --- | --- |
| II-1: | 2-Phenylnaphtho[1,8-bc]furan-5-one |
| II-2: | 2-(2-Methylphenyl)naphtho[1,8-bc]furan-5-one |
| II-3: | 2-(3-Methylphenyl)naphtho[1,8-bc]furan-5-one |
| II-4: | 2-(4-Methylphenyl)naphtho[1,8-bc]furan-5-one |
| II-5: | 2-(4-Ethylphenyl)naphtho[1,8-bc]furan-5-one |
| II-6: | 2(3,5-Dimethylphenyl)naphtho[1,8-bc]furan-5-one |
| II-7: | 2-(2-Methoxyphenyl)naphtho[1,8-bc]furan-5-one |
| II-8: | 2-(3-Methoxyphenyl)naphtho[1,8-bc]furan-5-one |
| II-9: | 2-(4-Methoxyphenyl)naphtho[1,8-bc]furan-5-one |
| II-10: | 2-(3,4-Dimethoxyphenyl)naphtho[1,8-bc]furan-5-one |
| II-11: | 2-(2,4-Dimethoxyphenyl)naphtho[1,8-bc]furan-5-one |
| II-12: | 2-(2-Chlorophenyl)naphtho[1,8-bc]furan-5-one |
| II-13: | 2-(3-Chlorophenyl)naphtho[1,8-bc]furan-5-one |
| II-14: | 2-(3-Bromophenyl)naphtho[1,8-bc]furan-5-one |
| II-15: | 2-(1-Naphthyl)naphtho[1,8-bc]furan-5-one |
| II-16: | 2-(2-Naphthyl)naphtho[1,8-bc]furan-5-one |
| II-17: | 2-(4-Isobutylphenyl)naphtho[1,8-bc]furan-5-one |
| II-18: | 2-(4-n-Butylphenyl)naphtho[1,8-bc]furan-5-one |
| II-19: | 2-(4-tert-Butylphenyl)naphtho[1,8-bc]furan-5-one |
| II-20: | 2-(2-Ethoxyphenyl)naphtho[1,8-bc]furan-5-one |

The 2-arylnaphtho[1,8-bc]furan-5-one can be used as a photopolymerization initiator for ethylenically unsaturated compounds solely or together with amine series photopolymerization accelerators (or auxiliary photopolymerization initiators).

In this invention, the ethylenically unsaturated compound is a compound having one or more addition polymerizable ethylenically unsaturated double bonds and it includes not only the monofunctional, difunctional, and trifunctional monomers which are the compounds having 1, 2, and 3 double bonds respectively described above but also oligomers which are polyfunctional, i.e., have 2 to 6 ethylenically unsaturated double bonds, and have molecular weights below about 10,000. The term "ethylenically unsaturated compounds" used herein includes compounds having a double bond(s) at the ends or in the midst of the main or side chains, but the ethylenically unsaturated compounds having a double bond(s) at the ends of the main or side chains are preferably used in the present invention. Also, the ethylenically unsaturated compound can be a mixture of aforesaid materials and a prepolymer where the ethylenically unsaturated double bonds of the mixture have been partially copolymerized.

In this invention, the preferred ethylenically unsaturated compounds have two or more ethylenically unsaturated double bonds in the molecule and in the preferred compounds, one and preferably most of the ethylenically unsaturated double bonds are in conjugation with and adjacent the carbon atom in a carbon to carbon double-bonded or a carbon-hetero atom (e.g., oxygen, nitrogen, sulfur, etc.) double bond. Particularly remarkable effects have been obtained using polymeric ethylenically unsaturated compounds when the double bond is in a conjugation with the carbonyl group of an ester or amide bond. As examples of these ethylenically unsaturated compounds, there are esters of unsaturated carboxylic acids and aliphatic polyols as shown below, and oligoester (or polyester) unsaturated carboxylates formed by ester-bonding of unsaturated carboxylic acids with the oligoesters (or polyesters) of polycarboxylic acids and aliphatic polyols.

Examples of the unsaturated carboxylic acid are acrylic acid, methacrylic acid, itaconic acid, crotonic acid, isocrotonic acid, and maleic acid.

Examples of the above-mentioned aliphatic polyols are ethylene glycol, triethylene glycol, tetraethylene glycol, tetramethylene glycol, neopentyl glycol, 1,10-decanediol, trimethylolethane, trimethylolpropane, 1,2-butanediol, 1,3-butanediol, propylene glycol, pentaerythritol, dipentaerythritol, tripentaerythritol, other poly-pentaerythritols, sorbitol, d-mannitol, dihydroxymaleic acid, etc.

Examples of esters of aliphatic polyols and unsaturated carboxylic acids are diacrylic acid ethylene glycol ester, triacrylic acid triethylene glycol ester, diacrylic acid 1,3-butanediol ester, diacrylic acid tetramethylene glycol ester, diacrylic acid propylene glycol ester, triacrylic acid trimethylolpropane ester, triacrylic acid trimethylolethane ester, trimethacrylic acid trimethylolpropane ester, trimethacrylic acid trimethylolethane ester, diacrylic acid tetraethylene glycol ester, diacrylic acid pentaerythritol ester, triacrylic acid pentaerythritol ester, tetraacrylic acid pentaerythritol ester, diacrylic acid dipentaerythritol ester, triacrylic acid dipentaerythritol ester, tetraacrylic acid dipentaerythritol ester, pentaacrylic acid dipentaerythritol ester, hexaacrylic acid dipentaerythritol ester, octaacrylic acid tripentaerythritol ester, tetraacrylic acid dipentaerythritol ester, pentaacrylic acid dipentaerythritol ester, hexaacrylic acid dipentaerythritol ester, octaacrylic acid tripentaerythritol ester, triacrylic acid sorbitol ester, tetraacrylic acid sorbitol ester, pentaacrylic acid sorbitol ester, hexaacrylic acid sorbitol ester, polyester acrylate oligomer, etc.

Examples of methacrylic acid ester are dimethacrylic acid tetramethylene glycol ester, dimethacrylic acid triethylene glycol ester, dimethacrylic acid pentaerythritol ester, trimethacrylic acid pentaerythritol ester, dimethacrylic acid dipentaerythritol ester, dimethacrylic acid pentaerythritol ester, trimethacrylic acid pentaerythritol ester, dimethacrylic acid dipentaerythritol ester, tetramethacrylic acid dipentaerythritol ester, octamethacrylic acid tripentaerythritol ester, dimethacrylic acid ethylene glycol ester, dimethacrylic acid 1,3-butanediol ester, dimethacrylic acid tetramethylene glycol ester, tetramethacrylic acid methylene glycol ester, etc.

Examples of itaconic acid ester are diitaconic acid ethylene glycol ester, diitaconic acid propylene glycol ester, diitaconic acid 1,3-butanediol ester, diitaconic acid 1,4-butanediol ester, diitaconic acid tetramethylene glycol ester, diitaconic acid pentaerythritol ester, triitaconic acid dipentaerythritol ester, pentaitaconic acid dipentaerythritol ester, hexaitaconic acid dipentaerythritol ester, tetraitaconic acid sorbitol ester, etc.

Examples of crotonic acid ester are dicrotonic acid ethylene glycol ester, dicrotonic acid propylene glycol ester, dicrotonic acid tetramethylene glycol ester, dicrotonic acid pentaerythritol ester, tetracrotonic acid sorbitol ester, etc.

Examples of isocrotonic acid ester are diisocrotonic acid ethylene glycol ester, diisocrotonic acid pentaerythritol ester, tetraisocrotonic acid sorbitol ester, etc.

Examples of maleic acid ester are dimaleic acid ethylene glycol ester, dimaleic acid triethylene glycol ester, dimaleic acid pentaerythritol ester, tetramaleic acid sorbitol ester, etc.

Then, examples of the oligoester (or polyester) unsaturated carboxylate are oligoester acrylate and oligoester methacrylate (hereinafter, they are referred to as oligoester (meth)acrylate, i.e., acrylate or methacrylate).

The oligoester (meth)acrylate is the reaction product obtained by the esterification reaction of acrylic acid or methacrylic acid, a polycarboxylic acid, and an aliphatic polyol and the compound is assumed to have the following general formula:

$$(CH_2=\overset{R^{10}}{\underset{|}{C}}-\overset{O}{\underset{\|}{C}}-O)_k E \qquad (XVI)$$

wherein $R^{10}$ represents a hydrogen atom or a methyl group; E represents an ester residue composed of an aliphatic polyol and a polycarboxylic acid and containing at least one ester bond; and k is an integer of 1 to 6.

Examples of the aliphatic polyol making up the ester residue E are, for example, polyols such as ethylene glycol, 1,2-propylene glycol, 1,4-butanediol, 1,6-hexanediol, trimethylolpropane, trimethylolmethane, 1,2,6-hexanetriol, glycerol, pentaerythritol, sorbitol, etc., and polyether type polyols such as diethylene glycol, triethylene glycol, tetraethylene glycol, decaethylene glycol, tetradecaethylene glycol, polyethylene glycol, dipropylene glycol, tripropylene glycol, tetrapropylene glycol, polypropylene glycol, etc.

On the other hand, the polycarboxylic acid making up the ester residue E are, for example, aromatic polycarboxylic acids such as phthalic acid, isophthalic acid, terephthalic acid, tetrachlorophthalic acid, tetrabromophthalic acid, trimellitic acid, pyromellitic acid, benzophenonedicarboxylic acid, etc., and saturated or unsaturated aliphatic polycarboxylic acids, such as malonic acid, succinic acid, glutaric acid, adipic acid, pimelic acid, sebacic acid, dodecanedioic acid, tetrahydrophthalic acid, maleic acid, fumaric acid, himic acid, itaconic acid, etc.

The ester residue E may be composed of one of the above-described aliphatic polyols and one of the polycarboxylic acids as well as two or more of one or both of the aforesaid polyols and polycarboxylic acids. Furthermore, the ester residue E may contain one molecule of the aforesaid aliphatic polyol and one molecule of the aforesaid polycarboxylic acid as well as two or more molecules of one or both of the aliphatic polyol and polycarboxylic acid. That is, any ester residue containing at least one ester bond can be used as E. The ester E generally has a molecular weight less than 10,000 and preferably less than 3,000. Also, the ester residue E includes one having remaining therein a hydroxyl group or one in which a hydroxyl group forms an ester with a monocarboxylic acid or has been substituted by an alkoxy group such as methoxy group and ethoxy group. Still further, the residue E may have a carboxyl group remaining therein.

The number of k in general formula (XVI) and the number of the ester bonds contained in E is usually 1 to 6. When k is 2 or more, an oligoester (meth)acrylate containing either of acryloyl group and methacryloyl group in one molecule may be used or an oligoester (meth)acrylate containing acryloyl group and methacryloyl group at any desired ratio in one molecule can be also used.

Practical examples of the oligoester (meth)acrylates used in this invention are illustrated in Table 2 as the assumed chemical structures but they represent only a part of the oligoester (meth)acrylates which may be used in this invention and other various oligoester (meth)acrylates can be also used in this invention. In Table 2, Y in the structural formulae represents acryloyl group ($CH_2$=CH—CO—) or methacryloyl group

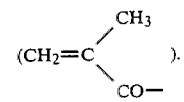

TABLE 2

Practical Examples of Oligoester (Meth)Acrylate

Y—OCH₂CH₂OOC—CH=CH—COOCH₂CH₂OH

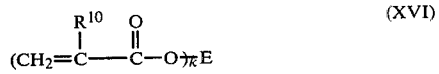
Y—OCH₂CH—OOC—CH₂CH₂—COO—CHCH₂OH (with CH₃ groups)

Y—O(CH₂CH₂O)$_z$OC—C₆H₄—CO(OCH₂CH₂)$_z$OH

Y(O(CH₂)$_\pi$OOC(CH₂)$_\pi$CO)$_z$O(CH₂)$_\pi$OOC—CH₃

Y—OCH₂CH₂OOC—C₆H₄—COOCH₂CH₂O—Y

Y(OCH₂CH₂OOC—C₆H₄—CO)$_z$OCH₂CH₂O—Y

Y—O(CH₂CH₂O)$_3$OC—CH=CH—CO(OCH₂CH₂)$_3$O—Y

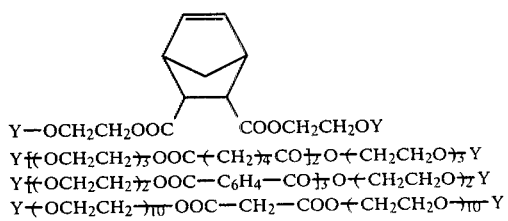

Y—OCH₂CH₂OOC   COOCH₂CH₂OY

Y(OCH₂CH₂)$_3$OOC(CH₂)$_\pi$CO)$_z$O(CH₂CH₂O)$_3$Y

Y(OCH₂CH₂)$_z$OOC—C₆H₄—CO)$_3$O(CH₂CH₂O)$_z$Y

Y(OCH₂CH₂)$_m$OOC—CH₂—COO(CH₂CH₂O)$_m$Y

TABLE 2-continued
Practical Examples of Oligoester (Meth)Acrylate
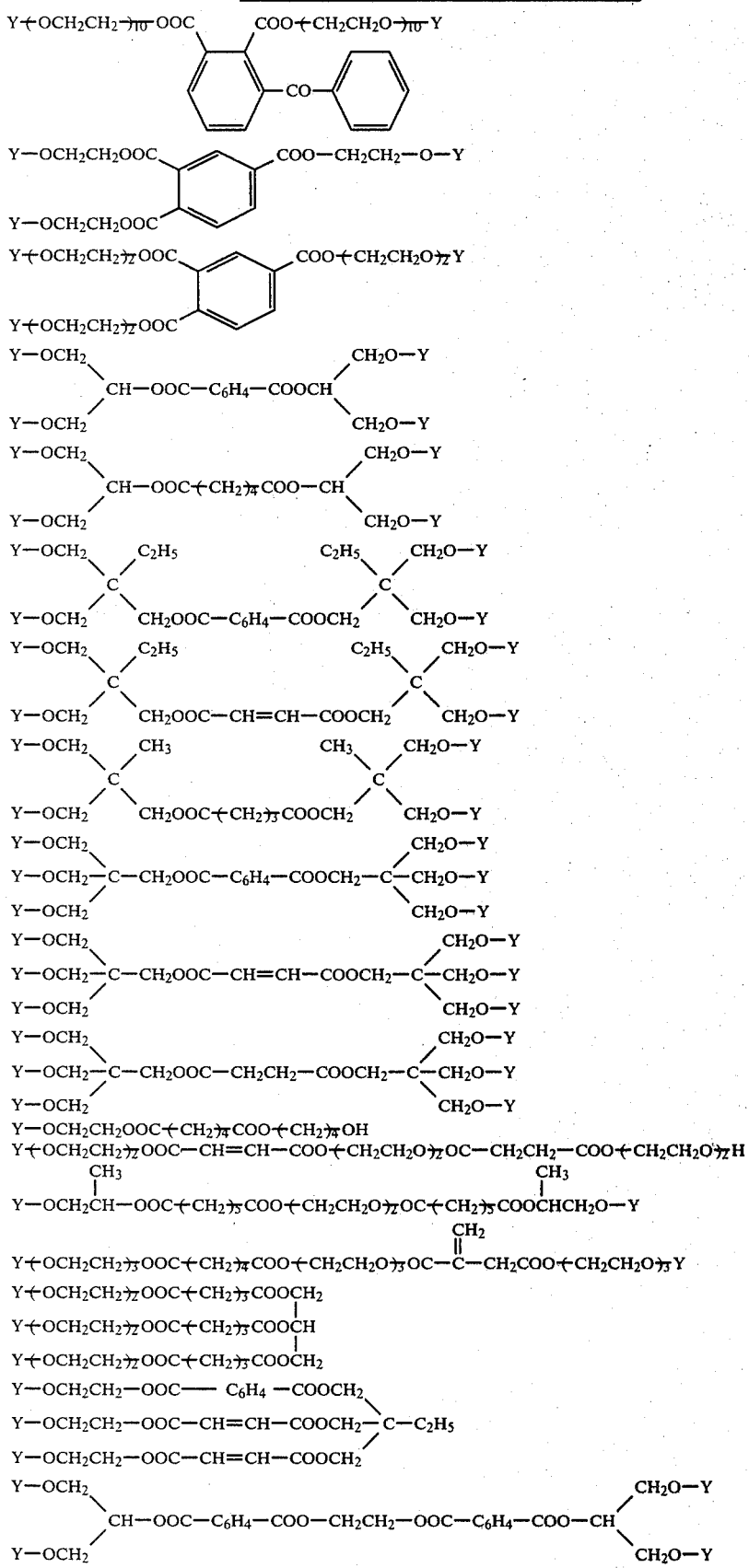

TABLE 2-continued
Practical Examples of Oligoester (Meth)Acrylate

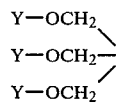
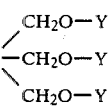

Y—OCH₂—C—CH₂OOC—CH=CH—COO(CH₂CH₂O)₃OC—CH=CH—COOCH₂—C—CH₂O—Y

In the invention, a very high-sensitive photopolymerizable composition is obtained by incorporating in the ethylenically unsaturated compound a 2-arylnaphtho[1,8-bc]-furan-5-one as only one component of the photopolymerization initiator (which may or may not include other initiators).

The 2-arylnaphtho[1,8-bc]furan-5-ones effective as photopolymerization initiator can be represented by above-mentioned general formula (II).

Among the compounds represented by formula (II), only the 2-phenylnaphtho[1,8-bc]furan-5-one wherein G' is an unsubstituted phenyl group is known. See D. H. Barton, B. Halpern, Q. N. Portar, and D. J. Collins, *Journal of Chemical Society* (C), 1971, 2166–2174. However, it must be emphasized that Barton et al report the compound, 2-phenylnaphtho[1,8-bc]furan-5-one only as a by-product of an intermediate formed in the synthesis of antibiotics. That is, previously it had not been known that the aforesaid compound is very effective as a photopolymerization initiator. The effectiveness of the compound as a photopolymerization initiator is based on the inventors' unexpected discovery.

The 2-arylnaphtho[1,8-bc]furan-5-ones (hereinafter, they are simply referred to as naphthofuranones) act as good photopolymerization initiators for ethylenically unsaturated compounds by themselves but when the naphthofuranones are used together with (c) an amine series photopolymerization accelerator (or an auxiliary photopolymerization initiator, a polymerization accelerator or a co-initiator), a photopolymerization initiator having synergistically increased sensitivity is obtained. The compounds effective as component (c), i.e., the amine series photopolymerization accelerator are the compounds represented by above-described general formulae (III), (IV), (V), (VI), (VII), (VIII), (IX), (X), (XI) or (XII) and these compounds give synergistic sensitization effect when used together with the component (b), naphthofuranone.

Now, examples of $R^1$, $R^2$ and $R^3$ in above-mentioned general formula (III) are straight chain, branched, and cyclic alkyl groups having 1 to 18 carbon atoms. Practical examples of the alkyl groups are methyl group, ethyl group, propyl group, butyl group, pentyl group, hexyl group, heptyl group, octyl group, nonyl group, decyl group, dodecyl group, octadecyl group, isopropyl group, isobutyl group, isopentyl group, isohexyl group, sec-butyl group, neopentyl group, tertbutyl group, tert-pentyl group, cyclopentyl group, cyclohexyl group, cycloheptyl group and 2-norbornyl group. Among these groups, the straight chain, branched, and cyclic alkyl groups having 1 to 10 carbon atoms are preferred.

Also, examples of the aryl group of $R^1$, $R^2$ and $R^3$ in general formula (III) are substituted or unsubstituted phenyl, naphthyl, anthryl, phenanthryl, biphenylyl, acenaphthenyl and indenyl, and the substituted aryl groups may be substituted with one, two or more substituents, which may be the same or different, such as a halogen atom (e.g., fluorine, chlorine, bromine, iodine), a nitro group, an amino group, a substituted amino group (e.g., monoalkyl-substituted amino group (examples of the alkyl group are a methyl group, an ethyl group, a propyl group, a pentyl group, an isopropyl group, a sec-butyl group, an isopentyl group), dialkylamino group (examples of the alkyl groups of which are the same as in case of the aforesaid monoalkyl-substituted amino group), monoacylamino group (examples of the acyl group are acetyl group, propionyl group, butyryl group, isobutyryl group, valeryl group, etc.)), a cyano group, an alkyl group (e.g., straight chain, branched chain and cyclic alkyl groups having 1 to 18 carbon atoms, preferably straight chain, branched chain and cyclic alkyl groups having 1 to 10 carbon atoms, practical examples of them having been described before), a halogenoalkyl group (e.g., chloromethyl group, 2-chloroethyl group, 5-chloropentyl group, trifluoromethyl group, etc.), an alkoxy group (examples of the alkyl group are methyl group, ethyl group, butyl group, pentyl group, isopropyl group, isopentyl group, 2-methylbutyl group, sec-butyl group, etc.), an aryloxy group (examples of the aryl group are phenyl group, 1-naphthyl group, 2-naphthyl group, etc.), an alkoxycarbonyl group (examples of the alkyl group are methyl group, ethyl group, propyl group, isopropyl group, butyl group, etc.), an acyloxy group (examples of the acyl group are those in above-mentioned monoacylamino group), an alkoxysulfonyl group (examples of the alkyl group are same as the examples of the alkyl group of the alkoxy group described above), etc.

Practical examples of these aryl groups are phenyl group, chlorophenyl group, a nitrophenyl group, aminophenyl group, (methylamino)phenyl group, (ethylamino)phenyl group, (dimethylamino)phenyl group, acetylaminophenyl group, tolyl group, ethylphenyl group, (chloromethyl)phenyl group, acetylphenyl group, phenoxyphenyl group, methoxycarbonylphenyl group, ethoxycarbonylphenyl group, acetoxyphenyl group, methoxysulfonylphenyl group, naphthyl group, 2-amino-1-naphthyl group, 1-dimethylamino-2-naphthyl group, chloronaphthyl group, methylnaphthyl group, anthryl group, phenanthryl group, indenyl group, biphenylyl group, chlorobiphenylyl group, aminobiphenylyl group, methylbiphenylyl group, and acenaphthenyl group. Among these groups, the residue of one benzene ring having one or two or more substituents, which may be the same or different, described above are preferred.

As examples of the aralkyl group of $R^1$, $R^2$ and $R^3$ in general formula (III) are the residues of straight chain, branched chain or cyclic alkyl groups having 1 to 10 carbon atoms, preferably 1 to 5 carbon atoms, each having a phenyl group or a naphthyl group as a substituent and practical examples of the aralkyl group are benzyl group, phenethyl group, 2-phenylpropyl group, 3-phenylhexyl group, 10-phenyldecyl group and 4-phenylcyclohexyl group.

Also, $R^1$, $R^2$ and $R^3$ in formula (III) further represent a substituted alkyl group and examples of the substituent are halogen atom (such as fluorine atom, chlorine atom, bromine atom, and iodine atom) and a hydroxyl group. On the other hand, as the alkyl group, there are straight chain, branched chain and cyclic alkyl groups having 1 to 18 carbon atoms, preferably 1 to 10 carbon atoms. Practical examples of the substituted alkyl group are chloromethyl group, bromomethyl group, 2-chloroethyl group, 2,2,2-trichloroethyl group, 2-chloropentyl group, 1-(chloromethyl)propyl group, 10-bromodecyl group, 16-methylheptadecyl group, chlorocyclohexyl group, hydroxymethyl group, 2-hydroxyethyl group, 2-hydroxybutyl group, 5-hydroxypentyl group, 10-hydroxydecyl group, 2-hydroxyoctadecyl group, 2-(hydroxymethyl)ethyl group, hydroxycyclohexyl group, 3-hydroxy-2-norbornyl group, etc.

Practical examples of the amines represented by general formula (III) are trimethylamine, triethylamine, tripropylamine, tributylamine, tripentylamine, tris(decyl)amine, methyldiethylamine, ethyldibutylamine, dimethyldecylamine, dimethylcyclohexylamine, diethylcyclohexylamine, N,N-dimethylaniline, N,N-diethylaniline, N,N-dimethylbenzylamine, N,N-diethylbenzylamine, N-benzyl-N-methylaniline, N-benzyl-N-ethylaniline, N-benzyl-N-propylaniline, N-phenethyl-N-methylaniline, N-phenethyl-N-ethylaniline, N,N-diphenylaniline, N,N-dibenzylaniline, triphenylamine, tribenzylamine, N,N-dimethyl-1-naphthylamine, N-methyldiphenylamine, trimethanolamine, triethanolamine, N-methyldiethanolamine, N,N-bis(2-hydroxyethyl)aniline, 1,1′,1″-nitrilotripropanol, 2,2′,2″-nitrilotripropanol, dimethylamine, diethylamine, dipropylamine, dibutylamine, dipentylamine, didecylamine, methylethylamine, ethylbutylamine, methylcyclohexylamine, ethylcyclohexylamine, N-methylaniline, N-ethylaniline, N-butylaniline, N-benzylaniline, N-phenethylaniline, diphenylamine, dibenzylamine, diphenethylamine, bis(hydroxymethyl)amine, diethanolamine, bis(3-hydroxypropyl)amine, N,N-bis(2,2-diethoxyethyl)methylamine, 2-(diisopropylamino)ethanol, 2-(N-ethyl-m-toluidino)ethanol, N,N-dimethyl-p-toluidine, N,N-bis(2-hydroxyethyl)-m-chloroaniline, 1-dimethylamino-2-propanol, 3-dimethylamino-1-propanol, 2-diethylaminoethanol, N-ethyl-N-(β-hydroxyethyl)aniline, etc.

In the practical examples described above, the compounds which show a particularly high synergistic effect and are most preferable are illustrated in Table 3.

TABLE 3

| Compound No. of Formula (III) | Name of Compound |
|---|---|
| III-1 | Triethanolamine |
| III-2 | N-Methyl-diethanolamine |
| III-3 | N,N-Bis(2-hydroxyethyl)aniline |
| III-4 | N,N-Dimethyl-1-naphthylamine |
| III-5 | N-Methyl-N-benzylaniline |
| III-6 | N-Ethyl-N-benzylaniline |
| III-7 | N-Methyl-diphenylamine |
| III-8 | N,N-Dimethyl-p-toluidine |
| III-9 | N,N-Bis(2-hydroxyethyl)-m-chloroaniline |

The above-mentioned amine compounds may be used as a mixture of two or more kinds thereof, although the use of one kind thereof gives a sufficient effect.

The substituents $R^4$ and $R^5$ of the p-dialkylaminoaromatic carbonyl compounds represented by general formulae (IV) to (IX) and general formula (XII), the p-dialkylaminoaromatic sulfone compounds represented by general formula (XI), and the p-dialkylaminostilbenes and the vinyl homologs represented by general formula (X) represent an alkyl group or a substituted alkyl group and they may be the same or different.

As the alkyl group, there are straight chain and branched chain alkyl groups having 1 to 18 carbon atoms and cyclic alkyl groups having 5 to 18 carbon atoms. Practical examples of the alkyl groups are methyl group, ethyl group, propyl group, butyl group, pentyl group, hexyl group, heptyl group, octyl group, nonyl group, decyl group, dodecyl group, octadecyl group, isopropyl group, isobutyl group, isopentyl group, isohexyl group, sec-butyl group, neopentyl group, tert-butyl group, tert-pentyl group, cyclopentyl group, cyclohexyl group, cycloheptyl group, 2-norbornyl group, α-decalyl group, β-decalyl group, etc. In these alkyl groups, the straight chain and branched chain alkyl groups having 1 to 10 carbon atoms and the cyclic alkyl groups having 6 to 10 carbon atoms are preferred.

As the substituents for the substituted alkyl groups, there are halogen atom (such as fluorine atom, chlorine atom, bromine atom, and iodine atom) and a hydroxyl group. On the other hand, as the alkyl groups, there are straight chain, branched chain and cyclic alkyl groups having 1 to 18 carbon atoms, preferably 1 to 10 carbon atoms. Practical examples of the substituted alkyl groups are chloromethyl group, bromomethyl group, 2-chloroethyl group, 2,2,2-trichloroethyl group, 2-chloropentyl group, 1-(chloromethyl)propyl group, 10-bromodecyl group, 16-methylheptadecyl group, chlorocyclohexyl group, hydroxymethyl group, 2-hydroxyethyl group, 2-hydroxybutyl group, 5-hydroxypentyl group, 10-hydroxydecyl group, 2-hydroxyoctadecyl group, 2-(hydroxymethyl)ethyl group, hydroxycyclohexyl group, 3-hydroxy-2-norbornyl group, etc.

The substituents $R^6$ of the p-dialkylaminoaromatic carbonyl compounds represented by general formulae (IV) and (V) and the p-dialkylaminoaromatic sulfone compounds represented by general formula (XI) represents an alkyl group, a substituted alkyl group, an alkoxy group, an aryl group, an aralkyl group, an aryloxy group, or a monovalent residue of a 5-membered or 6-membered heteroaromatic ring containing N, S or O. The alkyl group and the substituted alkyl group have the same definition as the alkyl group and substituted alkyl group of the above-described substituent $R^4$.

As the alkoxy group, there are alkoxy groups each having a straight chain, branched chain or cyclic alkyl group having 1 to 10 carbon atoms, preferably 1 to 5 carbon atoms. Practical examples of the alkoxy group are methoxy group, ethoxy group, propoxy group, butoxy group, pentyloxy group, hexyloxy group, nonyloxy group, decyloxy group, isopropoxy group, sec-butoxy group, tert-butoxy group, isopentyloxy group, cyclohexyloxy group, 2-norbornyloxy group, etc.

Examples of the aryl group are substituted or unsubstituted phenyl, naphthyl, anthryl, phenanthryl, biphenylyl, acenaphthenyl and indenyl, and the substituted ary groups may be substituted with one, two or more substituents which may be the same or different, such as halogen atom (such as fluorine atom, chlorine atom, bromine atom, and iodine atom), a nitro group, an amino group, a substituted amino group (a monoalkyl-substituted amino group (examples of the alkyl group are methyl group, ethyl group, propyl group, pentyl group, isopropyl group, sec-butyl group, isopentyl group, etc.), a dialkylamino group (examples of the alkyl group are same as those of the monoalkyl-substituted amino group described above), and a monoacylamino group (examples of the acyl group are acetyl group, propionyl group, butyryl group, isobutyryl group, valeryl group, etc.)), a cyano group, an alkyl group (straight chain, branched chain and cyclic alkyl groups having 1 to 18 carbon atoms, preferably 1 to 10 carbon atoms and practical examples of the alkyl groups are as described before), a halogenoalkyl group (such as chloromethyl group, 2-chloroethyl group, 5-chloropentyl group, trifluoromethyl group, etc.), an alkoxy group (examples of the alkyl group are methyl group, ethyl group, butyl group, pentyl group, isopropyl group, isopentyl group, 2-methylbutyl group, and sec-butyl group), an aryloxy group (examples of the aryl group are phenyl group, 1-naphthyl group, and 2-naphthyl group), an alkoxycarbonyl group (examples of the alkyl group are methyl group, ethyl group, propyl group, isopropyl group, and butyl group), an acyloxy group (examples of the acyl group are same as those of the monoacylamino group described before), and an alkoxysulfonyl group (examples of the alkyl group are same as those of the alkoxy group described above). In this case, the substituent may be one or two or more and in the latter case, the substituents may be the same or different. Practical examples of the aryl group are phenyl group, chlorophenyl group, aminophenyl group, (methylamino)phenyl group, (ethylamino)phenyl group, (dimethylamino)phenyl group, acetylaminophenyl group, tolyl group, ethylphenyl group, (chloromethyl)phenyl group, acetylphenyl group, phenoxyphenyl group, methoxycarbonylphenyl group, ethoxycarbonylphenyl group, acetoxyphenyl group, methoxysulfonylphenyl group, naphthyl group, 2-amino-1-naphthyl group, 1-dimethylamino-2-naphthyl group, chloronaphthyl group, methylnaphthyl group, anthryl group, phenanthryl group, indenyl group, biphenylyl group, chlorobiphenylyl group, aminobiphenylyl group, methylbiphenylyl group and acenaphthenyl group. In these aryl groups, the residue of one benzene ring having one or two or more, which may be the same or different, aforesaid substituents are preferred.

As aralkyl group, there are residues of straight chain, branched chain alkyl group having 1 to 10 carbon atoms, preferably 1 to 5 carbon atoms, or cyclic alkyl groups having 5 to 7 carbon atoms having a phenyl group or naphthyl group as substituent, and practical examples of the aralkyl groups are benzyl group, phenethyl group, 3-phenylpropyl group, 3-phenylhexyl group, 10-phenyldecyl group, 4-phenylcyclohexyl group, etc.

Also, as aryloxy group, there are phenoxy group, naphthyloxy group and biphenyloxy group.

Furthermore, as the monovalent residue of a heteroaromatic ring containing N, S or O, there are furyl group, benzofuryl group, pyrrolyl group, pyridyl group, indolyl group, thienyl group, and benzothienyl group.

The substituent $R^7$ of the p-dialkylaminoaromatic carbonyl compounds represented by general formula (XII) represents an alkyl group, an aryl group and an aralkyl group as defined for $R^6$ set forth above.

The substituents represented by X of the p-dialkylaminoaromatic carbonyl compounds represented by general formulae (VII) to (IX) and the p-dialkylaminostilbenes and the vinyl homologs represented by general formula (X) are substituents having Hammett's Σ value of from about −0.9 to about +0.7 and practical examples of which are hydrogen atom, methyl group, ethyl group, isopropyl group, tert-butyl group, phenyl group, trifluoromethyl group, cyano group, acetyl group, ethoxycarbonyl group, carboxyl group, carboxylato group (—COO⊖), amino group, methylamino group, dimethylamino group, ethylamino group, diethylamino group, acetylamino group, —PO₃H group, methoxy group, ethoxy group, propoxy group, isopropoxy group, butoxy group, pentyloxy group, phenoxy group, hydroxyl group, acetoxy group, methylthio group, ethylthio group, isopropylthio group, mercapto group, acetylthio group, thiocyano group (—SCN), methylsulfinyl group, ethylsulfinyl group, methylsulfonyl group, ethylsulfonyl group, aminosulfonyl group, dimethylsulfonio group (—S⊕(CH₃)₂), sulfonato group (—SO₃⊖), fluorine atom, chlorine atom, bromine atom and iodine atom. In these substituents, hydrogen atom, methyl group, ethyl group, methoxy group, ethoxy group, dimethylamino group, diethylamino group, chlorine atom, bromine atom, and cyano group are preferred.

The compounds represented by general formula (IV) are the compounds having p-di(substituted)alkylphenyl group and practical examples of them are shown in Table 4.

TABLE 4

| Compound No. of Formula (IV) | $R^4$ and $R^5$ | $R^6$ |
|---|---|---|
| IV-1 | —CH₃ | —CH₃ |
| IV-2 | —CH₃ | —C₂H₅ |
| IV-3 | —CH₃ | —CH₂CH₂CH₃ |
| IV-4 | —CH₃ | ─(CH₂)₁₀─CH₃ |
| IV-5 | —CH₃ | 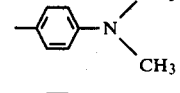 |
| IV-6 | —CH₃ |  |
| IV-7 | —CH₃ |  |
| IV-8 | —CH₃ | —CH₂CH₂— |
| IV-9 | —C₂H₅ | —CH₂CH₂CH₃ |
| IV-10 | —C₂H₅ |  |
| IV-11 | —C₂H₅ | 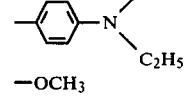 |
| IV-12 | —CH₃ | —OCH₃ |
| IV-13 | —CH₃ | —O—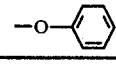 |

In the above compounds, the particularly preferred compounds are Compound Nos. (IV)-2, (IV)-3 (Michler's ketone), (IV)-5, and (IV)-8.

The compounds represented by general formula (V) are the compounds having p-dialkylaminocinnamoyl group and practical examples of these compounds are shown in Table 5.

TABLE 5

| Compound No. of Formula (V) | Name of Compound |
|---|---|
| V-1 | p-Dimethylaminostyryl methyl ketone |

TABLE 5-continued

| Compound No. of Formula (V) | Name of Compound |
|---|---|
| V-2 | p-Dimethylaminostyryl ethyl ketone |
| V-3 | p-Dimethylaminostyryl propyl ketone |
| V-4 | p-Dimethylaminostyryl butyl ketone |
| V-5 | p-Dimethylaminostyryl isobutyl ketone |
| V-6 | p-Dimethylaminostyryl tert-butyl ketone |
| V-7 | p-Dimethylaminostyryl heptyl ketone |
| V-8 | p-Dimethylaminostyryl undecyl ketone |
| V-9 | p-Dimethylaminostyryl cyclohexyl ketone |
| V-10 | p-Dimethylaminostyryl benzyl ketone |
| V-11 | p-Dimethylaminostyryl phenethyl ketone |
| V-12 | p-Dimethylaminocinnamic acid methyl ester |
| V-13 | p-Dimethylaminocinnamic acid ethyl ester |
| V-14 | p-Dimethylaminostyryl 2-pyridyl ketone |
| V-15 | p-Dimethylaminostyryl 4-pyridyl ketone |
| V-16 | p-Dimethylaminostyryl 2-thienyl ketone |
| V-17 | p-Dimethylaminostyryl 9-anthryl ketone |
| V-18 | p-Diethylaminostyryl methyl ketone |
| V-19 | P-Diethylaminostyryl ethyl ketone |
| V-20 | p-Diethylaminostyryl butyl ketone |
| V-21 | p-Dimethylaminostyryl 2-naphthyl ketone |

In the above-described practical examples, the preferred compounds and Compound Nos. (V)-1, (V)-2, (V)-3, (V)-4, (V)-5, (V)-6, (V)-9, (V)-10, (V)-11, (V)-12, (V)-13, (V)-15, (V)-16, (V)-17 and (V)-21.

In the p-dialkylaminoaromatic carbonyl compounds represented by general formula (VI), n is an integer of 3 to 8, preferably 3 or 4 and practical examples of them are shown in Table 6.

TABLE 6

| Compound No. of Formula (VI) | Name of Compound |
|---|---|
| VI-1 | 2-(p-Dimethylaminobenzylidene)cyclohexane |
| VI-2 | 2-(p-Dimethylaminobenzylidene)cyclopentanone |
| VI-3 | 2-(p-Diethylaminobenzylidene)cyclohexanone |
| VI-4 | 2-(p-Diethylaminobenzylidene)cyclopentanone |

Compounds (VI)-1 and (VI)-2 are particularly preferred in these compounds.

The p-dialkylaminoaromatic carbonyl compounds represented by general formula (VII) are p-dialkylaminochalcones and the derivatives thereof, and practical examples of them are shown in Table 7.

TABLE 7

| Compound No. of Formula (VII) | $R_4$ and $R^5$ | X |
|---|---|---|
| VII-1 | $-CH_3$ | $-H$ |
| VII-2 | $-CH_3$ | p-CN (represents $-CN$ group bonding to the p-position, and so forth) |
| VII-3 | $-CH_3$ | p-Cl |
| VII-4 | $-CH_3$ | m-Cl |
| VII-5 | $-CH_3$ | p-Br |
| VII-6 | $-CH_3$ | m-Br |
| VII-7 | $-CH_3$ | p-$CH_3$ |
| VII-8 | $-CH_3$ | m-$CH_3$ |
| VII-9 | $-CH_3$ | p-$C_2H_5$ |
| VII-10 | $-CH_3$ | m-$C_2H_5$ |
| VII-11 | $-CH_3$ | p-$OCH_3$ |
| VII-12 | $-CH_3$ | m-$OCH_3$ |
| VII-13 | $-CH_3$ | p-$OC_2H_5$ |
| VII-14 | $-CH_3$ | m-$OC_2H_5$ |
| VII-15 | $-CH_3$ | p-N(CH_3)(CH_3) |
| VII-16 | $-C_2H_5$ | p-CN |
| VII-17 | $-C_2H_5$ | m-Cl |
| VII-18 | $-C_2H_5$ | p-Cl |

TABLE 7-continued

| Compound No. of Formula (VII) | $R_4$ and $R^5$ | X |
|---|---|---|
| VII-19 | $-C_2H_5$ | m-Br |
| VII-20 | $-C_2H_5$ | p-Br |
| VII-21 | $-C_2H_5$ | p-$CH_3$ |
| VII-22 | $-C_2H_5$ | m-$C_2H_5$ |
| VII-23 | $-C_2H_5$ | p-$CH_3$ |
| VII-24 | $-C_2H_5$ | p-$OC_2H_5$ |
| VII-25 | $-C_2H_5$ | m-$OCH_3$ |
| VII-26 | $-C_2H_5$ | p-N($C_2H_5$)($C_2H_5$) |
| VII-27 | $-CH_3$ | p-OH |

In the above-described practical examples, the compounds preferably used are Compounds (VII)-1, (VII)-2, (VII)-3, (VII)-4, (VII)-5, (VII)-6, (VII)-7, (VII)-8, (VII)-9, (VII)-10, (VII)-11, (VII)-13, (VII)-15, (VII)-16, (VII)-17, (VII)-18, (VII)-19, (VII)-20, (VII)-26, and (VII)-27.

The p-dialkylaminoaromatic carbonyl compounds represented by general formula (VIII) are chalcone derivatives and practical examples of them are shown in Table 8.

TABLE 8

| Compound No. of Formula (VIII) | $R^4$ and $R^5$ | X |
|---|---|---|
| VIII-1 | $-CH_3$ | p-CN |
| VIII-2 | $-CH_3$ | p-Cl |
| VIII-3 | $-CH_3$ | m-Cl |
| VIII-4 | $-CH_3$ | m-Br |
| VIII-5 | $-CH_3$ | p-Br |
| VIII-6 | $-CH_3$ | m-$CH_3$ |
| VIII-7 | $-CH_3$ | p-$CH_3$ |
| VIII-8 | $-CH_3$ | m-$C_2H_5$ |
| VIII-9 | $-CH_3$ | p-$C_2H_5$ |
| VIII-10 | $-CH_3$ | m-$OCH_3$ |
| VIII-11 | $-CH_3$ | p-$OCH_3$ |
| VIII-12 | $-CH_3$ | m-$OC_2H_5$ |
| VIII-13 | $-CH_3$ | p-$OC_2H_5$ |
| VIII-14 | $-CH_3$ | p-N($C_2H_5$)($C_2H_5$) |
| VIII-15 | $-C_2H_5$ | p-$C_2H_5$ |
| VIII-16 | $-C_2H_5$ | m-$C_2H_5$ |
| VIII-17 | $-C_2H_5$ | p-$OCH_3$ |
| VIII-18 | $-C_2H_5$ | m-$OC_2H_5$ |

In the above practical examples, preferred compounds are Compounds (VIII)-1, (VIII)-2, (VIII)-3, (VIII)-4, (VIII)-5, (VIII)-6, (VIII)-7, (VIII)-9, (VIII)-11, (VIII)-13 and (VIII)-14.

The p-dialkylaminoaromatic carbonyl compounds represented by general formula (IX) are p-dialkylstyryl ketone derivatives and practical examples of them are shown in Table 9.

TABLE 9

| Compound No. of Formula (IX) | $R^4$ and $R^5$ | X |
|---|---|---|
| IX-1 | $-CH_3$ | p-CN |
| IX-2 | $-CH_3$ | p-Cl |
| IX-3 | $-CH_3$ | m-Cl |
| IX-4 | $-CH_3$ | p-Br |
| IX-5 | $-CH_3$ | m-Br |
| IX-6 | $-CH_3$ | H |
| IX-7 | $-CH_3$ | m-$CH_3$ |
| IX-8 | $-CH_3$ | p-$CH_3$ |
| IX-9 | $-CH_3$ | p-$C_2H_5$ |
| IX-10 | $-CH_3$ | m-$C_2H_5$ |

TABLE 9-continued

| Compound No. of Formula (IX) | R⁴ and R⁵ | X |
|---|---|---|
| IX-11 | —CH₃ | p-OCH₃ |
| IX-12 | —CH₃ | m-OCH₃ |
| IX-13 | —CH₃ | p-OC₂H₅ |
| IX-14 | —CH₃ | p-N(CH₃)(CH₃) |
| IX-15 | —C₂H₅ | p-CN |
| IX-16 | —C₂H₅ | p-Br |
| IX-17 | —C₂H₅ | m-Cl |
| IX-18 | —C₂H₅ | H |
| IX-19 | —C₂H₅ | p-CH₃ |
| IX-20 | —C₂H₅ | m-C₂H₅ |
| IX-21 | —C₂H₅ | p-OCH₃ |
| IX-22 | —C₂H₅ | m-OC₂H₅ |
| IX-23 | —C₂H₅ | p-N(C₂H₅)(C₂H₅) |

In the practical examples, the preferred compounds are compounds (IX)-1, (IX)-2, (IX)-3, (IX)-4, (IX)-5, (IX)-6, (IX)-8, (IX)-9, (IX)-11, (IX)-13, (IX)-14, and (IX)-23.

Also, the amine series photopolymerization accelerators represented by general formula (X) are p-dialkylaminostilbenes and the vinyl homologs thereof and practical examples of them are shown in Table 10.

TABLE 10

| Compound No. of Formula (X) | R₄ and R₅ | m | X |
|---|---|---|---|
| X-1 | —CH₃ | 1 | p-CH₃ |
| X-2 | —CH₃ | 1 | p-Cl |
| X-3 | —CH₃ | 1 | p-N(CH₃)(CH₃) |
| X-4 | —C₂H₅ | 1 | H |
| X-5 | —CH₃ | 2 | H |

The compounds represented by general formula (XI) are p-dialkylaminostyryl sulfones and practical examples of them are shown in Table 11.

TABLE 11

| Compound No. of Formula (XI) | R⁴ and R⁵ | R⁶ |
|---|---|---|
| XI-1 | —CH₃ | —CH₃ |
| XI-2 | —CH₃ | —C₂H₅ |
| XI-3 | —CH₃ | —C₆H₅ |
| XI-4 | —CH₃ | —C₆H₄CH₃ |

Furthermore, the compounds represented by general formula (XIII) are p-dialkylaminophenylethelidene compounds and practical examples of them are shown in Table 12.

TABLE 12

| Compound No. of Formula (XII) | R⁴ and R⁵ | R⁷ |
|---|---|---|
| XII-1 | —CH₃ | —CH₃ |
| XII-2 | —CH₃ | —C₂H₅ |
| XII-3 | —CH₃ | —CH₂CH₂CH₃ |

TABLE 12-continued

| Compound No. of Formula (XII) | R⁴ and R⁵ | R⁷ |
|---|---|---|
| XII-4 | —CH₃ | —C(CH₃)(CH₃)(CH₃) |

Moreover, some polyamine compounds show synergistic photopolymerization accelerating effect and practical examples of these polyamine compounds are methylenediamine, ethylenediamine, trimethylenediamine, tetramethylenediamine, pentamethylenediamine, hexamethylenediamine, decamethlenediamine, propylenediamine, butylenediamine, 1,4-cyclohexanediamine, phenylenediamine, (2-aminomethylbutyl)amine, triethylenetetramine, and hexamethylenetetramine.

Now, the production processes of the above-mentioned p-dialkylaminoaromatic compounds will be explained. For example, a p-dimethylaminostyryl propyl ketone can be produced by the condensation reaction of a p-dimethylaminobenzaldehyde and propyl ether ketone (so-called Perkin's reaction) and also a p-dimethylaminochalcone can be produced by the condensation reaction of a p-dimethylaminobenzaldehyde and phenyl methyl ketone (Perkin's reaction, etc.). Practically speaking, the compounds of general formulae (III) to (VII) can be produced by the process of O. Pfeiffer & O. Angen, *Justus Liebigs Annalen der Chemie*, Vol. 44, 228–265 (1925), the process of B. N. Dashkevich & I. V. Smedanks, *Ukrain. Khim. Zhur.*, Vol. 21, 619–624 (1955), and the process of I. V. Smedanka, *Nauch. Zapjski. Uzhgrod. Univ.*, Vol. 18, 15–19 (1955).

When a photopolymerizable composition comprising, as the initiator, the naphthofuranone (b) and a p-dialkylaminoaromatic carbonyl compound represented by general formula (IX) described above (c) is imagewise exposed, discoloring of the photopolymerization accelerator (c) frequently occurs. The explanation for this is not clear but the effect is particularly remarkable only for the compounds represented by general formula (IX) of the p-dialkylaminoaromatic compounds represented by general formulae (III) to (XII). By this feature, when the layer of a photosensitive material containing the compound represented by general formula (IX) is imagewise exposed, the coloration is reduced at the exposed portions to give a positive image.

It is described in Anthony J. Been et al., Japanese Patent Application (OPI) No. 110,781/1974 (corresponding to U.S. patent application Ser. No. 328,442, filed Jan. 31, 1973) that when a compound of an element belonging to the periodic table, group V is used together with an ethylenically unsaturated compound in case of using a carbonyl group-containing compound as the photopolymerization initiator, the sensitivity of the photopolymerization increases. The combination of the naphthofuranone (b) and the amine series photopolymerization accelerator (c) in this invention is completely different than the invention of the Been et al application in the specific initiator combination used and the superiority of the effect which is obtained. That is, the 2-arylnaphtho[1,8-bc]furan-5-ones have a partial structure wherein one of the carbonyl groups of 1,4-naphthoquinone is involved in an oxo-methylene bond but it has not yet been known that the compounds belong to so-called 1,4-naphthoquinone methide having the aforesaid structure are very effective as photopolymerization initiator as well as is based on the inventors' unexpected discovery.

Furthermore, the effect of the combination of this invention is particularly remarkable as compared with conventional combinations in the point that the amine series photopolymerization accelerator (c) defined in this invention shows a very high synergistic action for the carbonyl group-containing compounds.

Also, the presence of the dialkylamino group which characterizes the preferred examples of the compound (c) is insufficient to predict the synergism of the combination of the two components of the photopolymerization initiators used in the present invention. For example, when the following compounds are used together with the compound (b), no synergism is obtained in the case of using Compounds a or b and, quite to the contrary, the effect is reduced in the case of using Compounds c, d or e.

Compound a:

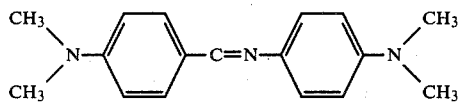

Compound b:

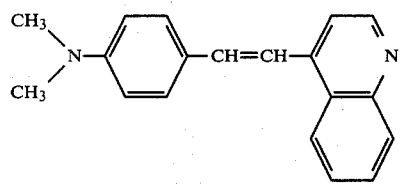

Compound c:

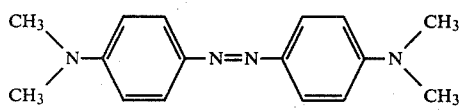

Compound d:

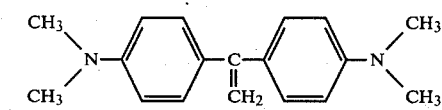

Compound e:

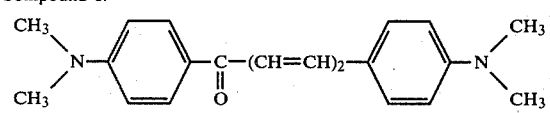

Therefore, it would not be expected that the synergistic acceleration effect would be detained with the naphthofuranone.

The amount of the photopolymerization initiator, 2-arylnaphtho[1,8-bc]furan-5-one (b) which can be used in the photopolymerizable composition of this invention is in a wide range of from about 1/5 to about 1/1,000 by weight ratio to the ethylenically unsaturated compound. Usually, the highest photopolymerization (photo-hardening) sensitivity is obtained in the range of from about 1/10 to about 1/100 by weight and, hence, it is preferred to use the photopolymerization initiator (b) and the ethylenically unsaturated compound in this range. In general, as the amount of the naphthofuranone increases gradually from zero, the sensitivity of the composition increases gradually and, in many cases, decreases again after passing through a maximum value. (Some of the compositions reach saturation before the sensitivity of them begins to increase.) Therefore, when the highest sensitivity is not required (for example, when the strength, flexibility, durability against etching, etc., are more important than sensitivity and in those cases in which it is difficult to control exposure due to too high sensitivity), other ranges than the above-stated preferred range may be employed. Furthermore, in the case of using the naphthofuranone (b) together with the nitrogen compound, the amine series photopolymerization accelerator (c), the acceleration effect is obtained with the mol ratio of the both components being from about 20/1 to about 1/20 but since the highest acceleration effect is obtained in the range of from about 4/1 to about ¼, it is preferred to use the components in the latter range, although they can be used in other amounts than the above-indicated ranges with a photopolymerization acceleration effect. Total amount of components (b) and (c) ranges from about 0.1 to about 10% by weight, preferably from about 0.2 to 7% by weight, based on the weight of the monomer(s) used.

The photopolymerizable composition of this invention containing the above-mentioned ethylenically unsaturated compound and photopolymerization initiator may further contain, if necessary, known additives such as binders, thermal-polymerization inhibitors, plasticizers, coloring agents, surface smoothening agents, etc.

For forming a resist image on a support as in the photosensitive materials for performing development by stripping or the photosensitive materials for performing liquid development as will be described later, it is preferred to use film-forming polymer (binder) with the composition. In this case, any organic polymer can be used as long as it is compatible with the ethylenically unsaturated compounds. It is desirable to select a polymer which is suitable for development by stripping, water development, or weak alkaline solution development. The organic polymer which is a film-forming agent for the aforesaid photopolymerizable composition as well as is soluble in or swellable by water, weak alkaline aqueous solution, or an organic solvent used for development can be selectively used. For example, when a water-soluble organic polymer is used, water development can be used. Examples of such organic polymers are addition polymers having carboxyl groups in the side chain, such as a methacrylic acid copolymer, an acrylic acid copolymer, an itaconic acid copolymer, a partially esterified maleic acid copolymer, a maleic acid copolymer, a crotonic acid copolymer, etc., and also acid cellulose derivatives having carboxyl group at the side chain. In addition to the above-illustrated materials, cyclic acid anhydride-added addition polymers having hydroxyl group can be also used. Still other examples of the water-soluble organic polymers are polyvinyl pyrrolidone and polyethylene oxide. Also, alcohol-soluble nylon and a polyether of 2,2-bis(4-hydroxyphenyl)propane and epichlorohydrin are useful for increasing the strength of film of the hardened parts after exposure. These water-soluble polymers are well known in the art.

The organic polymer may be incorporated in the photopolymerizable composition in any desired proportion but if the proportion of the organic polymer is over 90% by weight, the preferred result is not obtained from the standpoint of strength of images formed, etc.

Examples of the linear organic polymer for use in stripping development are chlorinated polyolefins having a chlorine content of from about 60% by weight to about 75% by weight, such as chlorinated polyethylene, chlorinated polypropylene, etc.; copolymers of acrylic acid alkyl ester (examples of the alkyl group are methyl group, ethyl group, butyl group, etc.) and at least one of the monomers such as acrylonitrile, vinyl chloride, vinylidene chloride, styrene, butadiene, etc., such as polymethyl methacrylate, polyacrylic acid, polymethacrylic acid, polyacrylic acid alkyl ester (examples of the alkyl group are same as above; and such homopolymers and copolymers as polyvinyl chloride, a copolymer of vinyl chloride and acrylonitrile, polyvinylidene chloride, a copolymer of vinylidene chloride and acrylonitrile, polyvinyl acetate, a copolymer of vinyl acetate and vinyl chloride, polyvinyl alcohol, polyvinyl pyrrolidone, polyacrylonitrile, a copolymer of acrylonitrile and styrene, an interpolymer of acrylonitrile, butadiene, and styrene, a polyvinyl alkyl ether (examples of the alkyl group are methyl group, ethyl group, isopropyl group, butyl group, etc.), polymethyl vinyl ketone, polyethyl vinyl ketone, polyethylene, poly-α-methylstyrene, polyamide (6-nylon, 6,6-nylon, etc.), poly-1,3-butadiene, polyisoprene, polyurethane, polyethylene terephthalate, polyethylene isophthalate, chlorinated rubber, polychloroprene, ethyl cellulose, acetyl cellulose, polyvinyl putyral, polyvinyl formal, styrene-butadiene rubber, chlorosulfonated polyethylene, etc. In case of copolymers, the ratio of the component monomers may be in a wide range but generally it is preferred that the proportion of the component of smaller monomer be in a range of 10 to 50% by mol ratio. Also, thermoplastic polymers having the monomer ratio other than the aforesaid range can be used in this invention if they meet the above-mentioned conditions.

In the above-illustrated polymers, the materials suitably used together with the photopolymerizable compositions of this invention are chlorinated polyethylene having a chlorine content of from about 60% by weight to about 75% by weight, chlorinated polypropylene having the same chlorine content as above, polymethyl methacrylate, polyvinyl chloride, a copolymer of vinyl chloride and vinylidene chloride (content of vinyl chloride is 20% to 80% by mol), a copolymer of vinylidene chloride and acrylonitrile (content of acrylonitrile is 10 to 30% by mol), a copolymer of vinyl chloride and acrylonitrile (content of acrylonitrile is 10 to 30% by mol), polystyrene, polyvinyl butyral, polyvinyl acetate, polyvinyl formal, ethyl cellulose, acetyl cellulose, a copolymer of vinyl chloride and vinyl acetate, polychloroprene, polyisoprene, chlorinated rubber, chlorosulfonated polyethylene, etc.

These polymers may be used alone but, to simplify the preparation of the coating composition, they may also be used as an admixture of two or more polymers in the proper mixing ratio which does not cause demixing during the steps before coating and drying.

Practical examples of conventional thermal polymerization inhibitors are p-methoxyphenol, hydroquinone, alkyl-substituted hydroquinone, aryl-substituted hydroquinone, 1-butylcatechol, pyrogallol, cuprous chloride, phenothiazine, chloranil, naphthylamine, β-naphthol, 2,6-di-t-butyl-p-cresol, pyridine, nitrobenzene, dinitrobenzene, p-toluidine, methylene blue, copper salts of organic acids (e.g., copper acetate), etc. It is preferred that the thermal polymerization inhibitor be incorporated in the above-mentioned ethylenically unsaturated compound in an amount of from 0.001 part by weight to 5 parts by weight per 100 parts by weight of the ethylenically unsaturated compound. That is, the thermal polymerization inhibitor can be used in this invention for increasing the stability with time of the composition of this invention before exposure.

As the coloring agents, there are illustrated, for example, pigments such as titanium oxide, carbon black, iron oxide, phthalocyanine series pigments, azo series pigments, etc., and dyes such as methylene blue, Crystal Violet, Rhodamine B, Fuchsine, Auramine, azo series dyes, anthraquinone series dyes, etc. A condition for using the coloring agents, however, is that the coloring agent not absorb light of the wavelengths matching the absorption wavelengths of the photopolymerization initiator. It is preferred that the coloring agent be incorporated in the photopolymerizable composition in an amount of 0.1 to 30 parts by weight per 100 parts by weight based on the sum of the binder and the ethylenically unsaturated compound in case of the pigment and in an amount of 0.01 to 10 parts by weight, preferably 0.1 to 3 parts by weight for the dye. In the case of incorporating the above-mentioned coloring agent, it is preferred to use a chlorinated fatty acid such as dichloromethyl stearate as an adjuvant for the coloring agent and the amount of the adjuvant is usually from 0.005 to 0.5 part by weight per 1 part by weight of the coloring agent. However, when the photopolymerizable composition of this invention contains a plasticizer, the adjuvant for the coloring agent is unnecessary. Examples of the plasticizers are phthalic acid esters such as dimethyl phthalate, diethyl phthalate, dibutyl phthalate, diisobutyl phthalate, dioctyl phthalate, octylcapryl phthalate, dicyclohexyl phthalate, ditridecyl phthalate, butylbenzyl phthalate, diisodecyl phthalate, diallyl phthalate, ect.; glycol esters such as dimethyl glycol phthalate, ethylphthalyl ethyl glycolate, methylphthalyl ethyl glycolate, triethylene glycol dicapric acid ester, etc.; phosphoric acid esters such as tricresyl phosphate, triphenyl phosphate, etc.; aliphatic dibasic esters such as diisobutyl adipate, dioctyl adipate, dimethyl sebacate, dibutyl sebacate, dioctyl azelate, dibutyl maleate, etc.; triethyl citrate; glycerol triacetyl ester; butyl laurate; etc.

As examples of the surface smoothening agent, there are lanolin, paraffin wax, natural wax, etc.

The above modifiers can be used, if necessary, in the photopolymerizable compositions of this invention in a total amount of up to 3% by weight, preferably 1% by weight to the composition.

In the most general mode of using the photopolymerizable composition of this invention, a coating solution of the photopolymerizable composition is prepared by dissolving the composition in a solvent, coating on a support by a conventional means, and then the solvent is removed to provide a photopolymerizable photosensitive material.

Examples of the solvent are ketones such as acetone, methyl ethyl ketone, methyl isobutyl ketone, cyclohexanone, diisobutyl ketone, etc.; esters such as ethyl acetate, butyl acetate, n-amyl acetate, methyl formate, a propionic acid ester, dimethyl phthalate, ethyl benzoate, etc.; aromatic hydrocarbons such as toluene, xylene, benzene, ethylbenzene, etc.; halogenated hydrocarbons such as carbon tetrachloride, trichloroethylene, chloroform, 1,1,1-trichloroethane, monochlorobenzene, chloronaphthalene, etc.; ethers such as tetrahydrofuran, diethyl ether, ethylene glycol monomethyl ether, ethylene glycol monoethyl ether acetate, etc.; dimethylformamide; and dimethyl sulfoxide.

As the support onto which the photopolymerizable composition of this invention is applied in a suitable form (for example, the form of liquid composition as described above), there are planar or other materials which do not cause marked dimensional deformation. Examples of the flat material are glass, silicon oxide, ceramics, papers, metals (e.g., aluminum, zinc, magnesium, copper, iron, chromium, nickel, silver, gold, platinum, palladium, an aluminum-base alloy, a zinc-base alloy, a magnesium-base alloy, a copper-zinc alloy, an iron-nickel-chromium alloy, a copper-base alloy, etc.), metal compounds (e.g., aluminum oxide, tin oxide ($SnO_2$), indium oxide ($In_2O_3$)), and polymers (e.g., regenerated cellulose, cellulose nitrate, cellulose diacetate, cellulose triacetate, cellulose acetate butyrate, cellulose acetate propionate, polystyrene, polyethylene terephthalate, polyethylene isophthalate, the polycarbonate of bisphenol A, polyethylene, polypropylene, nylon such as 6-nylon, 6,6-nylon, 6,10-nylon, etc., polyvinyl chloride, a vinyl chloride-vinyl acetate copolymer, a vinyl chloride-acrylonitrile copolymer, a vinyl chloride-vinylidene chloride copolymer, polyacrylonitrile, methyl polyacrylate, methyl polymethacrylate, etc.).

Also, laminates of the aforesaid materials such as cermet, iron-aluminum laminated plates, iron-copper-aluminum laminated plates, iron-chromium-copper laminated plates, polyethylene-coated papers, cellulose triacetate-coated papers, an aluminum plate having on the surface thereof a layer of aluminum oxide formed by anodically oxidizing the surface of the plate, a chromium plate having a layer of chromium oxide formed by a conventional manner, a glass plate having formed on the surface a layer of tin oxide, a silicon oxide plate having formed on the surface a layer of indium oxide, etc., can be used as the support.

Furthermore, a transparent support or opaque support may be selected from these materials according to the purpose of the photosensitive image-forming materials to be formed using the photopolymerizable compositions of this invention. In the case of using transparent support, it is possible to use not only a colorless transparent support but also a colored transparent support containing a dye or pigment as described in *J. SMPTE*, Vol. 67, 296 (1958). In the case of opaque support, not only originally opaque supports such as paper and metal but also an opaque support prepared by incorporating titanium oxide or other proper pigment or dye in a transparent material, a plastic film surface-treated by the method as described in British Pat. No. 1,237,475, a paper or plastic film provided with complete light-shading property by the addition of carbon black, etc., can be also used. Moreover, a support having finely matted surface by the treatment of sand-graining, electrolytic etching, anodic oxidation, chemical etching, etc., as well as a support pre-treated with corona discharging, ultraviolet irradiation, flame treatment, etc., can be used. Still further, a plastic support reinforced by mixing therein a reinforcing material such as glass fibers, carbon fibers, boron fibers, various metallic fibers, metallic whiskers, etc., may be also used in this invention.

Also, if necessary, the support used in this invention may have thereon other layers such as an antihalation layer, an ultraviolet absorbing layer, a visible ray absorbing layer, etc.

To prevent the reduction in photopolymerization rate (sensitivity) of the photopolymerizable composition of this invention by the action of oxygen, the photosensitive material composed of the photopolymerizable composition may be imagewise exposed using the vacuum printing frame as described in U.S. Pat. No. 3,060,026, or a transparent cover which can be removed may be formed on the photosensitive material, or further a coating having less oxygen permeability may be formed on the photosensitive layer of the photosensitive material as described in U.S. Pat. No. 3,203,805.

Factors which determining the speed that the photopolymerizable composition of this invention is photopolymerized, hardened, and dried include the properties of the support particularly the surface thereof, the specific components of the photopolymerizable composition, the content of the photopolymerization initiator in the whole photopolymerizable composition, the thickness of the layer of the photopolymerizable composition, the properties and intensity of the light source (e.g., properties of emission spectra), the presence or absence of oxygen, and the temperature of surrounding atmosphere. The light irradiation may be practiced in any one or combination of manners. For example, the composition may be exposed to any actinic light obtained by any type of light source if the light source can give effective exposure amount. The absorption maximum of the 2-arylnaphtho[1,8-bc]furanone of this invention at the longer wavelength side is in 380 to 430 nm (molecular extinction coefficient about $10^4$ $l \cdot mol^{-1} \cdot cm^{-1}$) and the longer wavelength end of the absorption extends to 460 to 500 nm. Also, the absorption maximum at a longer wavelength side of the p-dialkylamino-aromatic carbonyl compound among the nitrogen compounds which can achieve the remarkable increase in light sensitivity when used together with the naphthofuranone is in 380 to 420 nm and the absorption thereof reaches about 500 nm. The wavelength region effective for hardening the photopolymerizable composition of this invention is from 180 nm ultraviolet spectrum to about 600 nm in the visible spectrum. Light sources having spectral energy distribution in this region can be effectively used in this invention. However, the composition of this invention is also sensitive to electromagnetic waves of shorter wavelengths in the range of vacuum ultraviolet rays, X-rays, and gamma rays as well as particle rays such as electron rays, neutron rays, and alpha rays and, hence, they can be utilized for the image exposure of the photopolymerizable composition of this invention. Examples of the proper light sources for ultraviolet rays and visible rays are a carbon arc lamp, mercury vapor lamp, xenon lamp, fluorescent lamp, argon glow discharge lamp, photographic flood lamp, and van de Graaff accelerator.

The light irradiation or exposure must be conducted for a time sufficient to provide the effective exposure amount, generally about 1 to about 60 seconds, preferably about 2 to about 30 seconds. The exposure time is determined within the above range by adjusting the light intensity of the light source and the distance between the light source and the photopolymerizable composition such that effective light exposure amount is achieved. The light exposure may be performed at any practical temperature but it is most desirable for practical reasons to perform the light exposure at room temperature, i.e., from 10° C. to 40° C.

The hardened composition is in a dry state and exhibits elasticity. The hardened composition also shows abrasion resistance and chemical resistance and possesses excellent ink receptivity, stain-dissolving property, and printing out property as well as possesses adaptability for pre-sensitized relief or lithographic printing materials and for photoresists. As a matter of course, the composition of this invention can be used for photosensitive printing inks; light-hardenable adhesives for metallic foils, films, papers, fabrics, etc.; light-hardenable coating materials for metals, plastics, papers, woods, metallic foils, fabrics, glasses, boards, cardboards for making boxes; and light-hardenable marks or signals for roads, parking places, and air terminals.

When the composition of this invention is used as, for example, a vehicle for printing, the composition may be colored by a known amount of dye and at the same time by various known organic pigments such as Molybdate Orange, titanium white, Chromium Yellow, Phthalocyanine Blue, and carbon black. In this case, the possible amount of the vehicle used is from about 20% to 99.9% by weight to the whole weight of the composition and the amount of the coloring agent is from about 0.1% to 80% by weight. The materials which can be printed include papers, clay-coated papers, and cardboards for making boxes.

The composition of this invention is further suitable for the treatment of fabrics from natural and synthetic fibers. For example, the composition can be used in a vehicle for rendering fabrics waterproof, oil resistant, stain resistant, bending strength, etc., as well as in vehicles of printing inks for cloths.

Furthermore, the photopolymerizable (light-hardenable) composition of this invention can also be used as a coating materials for coating or printing on the surfaces of metals, glasses or plastics by a roller system or spray system. In the case of coating glasses, polyester films, vinyl polymer films, polymer-coated cellophane, treated or untreated polyethylene used, for example, as cups or bottles, treated or untreated polypropylene, etc., with the composition of this invention, a coloring coating method may be employed. Tin plate subjected or not subjected to sizing can be also used as metals to which the composition of this invention is applicable.

The photopolymerizable photosensitive image-forming material prepared using the photopolymerizable or light-hardenable composition of this invention usually comprises a sheet-like or plate-like support having formed thereon a layer of the photopolymerizable composition of this invention as a photosensitive element.

In one embodiment, photosensitive image-forming materials based on the composition of this invention comprise a layer of the composition of this invention formed on the surface of a support and further a transparent plastic film formed on the composition layer. With this construction, the photosensitive material can be used after stripping the transparent plastic film directly before image exposure or alternatively the photosensitive image-forming material with the transparent plastic film may be imagewise exposed through the transparent plastic film or through the support when the support is transparent and thereafter, the transparent plastic film is stripped to leave the exposed and hardened portions of the composition layer on the support while the unexposed and unhardened portions thereof remain on the surface of the plastic film (or the exposed and hardened portions of the composition remain on the transparent plastic film while the unexposed and unhardened portions remain on the support). That is, the composition of this invention can be particularly profitably used as materials for so-called splitting off (or peeling-apart) developing type photosensitive materials.

In the photosensitive image-forming material using the photopolymerizable composition of this invention, the image exposure is accomplished by exposing specific portions of the layer of the photopolymerizable composition to light until the addition polymerization reaction of the exposed portions reaches a desired thickness and/or hardness. Then, the unexposed portions of the composition layer are removed by treating them with a solvent which dissolves only the unhardened portions composed of the unreacted ethylenically unsaturated compound (monomer, oligomer, or prepolymer) without dissolving the light-hardened portions or they are removed by stripping development. When using the photopolymerizable composition of this invention as a photosensitive image-forming material, the thickness of the layer of the composition after removing (or evaporating) the solvent (or drying) is from 0.5 $\mu$m to 150 $\mu$m, preferably from 1 $\mu$m to 100 $\mu$m. The flexibility decreases as the thickness of the composition layer increases and the abrasion resistance decreases as the thickness of the composition layer decreases.

When the composition of this invention is used as a printing ink, coating composition, and adhesive, the composition can be used without using a volatile solvent. In this case, the printing ink, coating composition, etc., has the advantages of a non-solvent system, which are not observed in conventional oil-containing resin type or solvent type ink or coating material.

When a combination of the naphthofuranone of this invention and an oxidizable leuco dye is exposed to light, a colored image can be obtained. Here, the "leuco dye" is an oxidizable dye which is capable of being oxidized by triarylimidazolyl radical, etc., known oxidizing agents for forming colored dye.

Examples of the leuco dye are, for example, aminotriarylmethanes, aminoxanthenes, aminothioxanthenes, amino-9,10-dihydroacridines, aminophenoxazines, aminophenothiazines, aminodihydrophenazines, aminodiphenylmethanes, leucoindamines, aminohydrocinnamic acids, hydrazines, leucoindigoid dyes, and amino-2,3-dihydroanthraquinones as described in U.S. Pat. Nos. 3,445,234, 3,423,427, 3,449,379, 3,395,018 and 3,390,997.

Typical examples of the aforesaid aminotriarylmethanes are tris(p-diethylaminophenyl)methane, tris(4-diethylamino-o-toluyl)methane, bis(4-diethylamino-o-toluyl) (p-benzylthiophenyl)methane, bis(4-diethylamino-o-toluyl) (2,4-dimethoxyphenyl)methane, and bis(4-diethylamino-o-toluyl) (p-chlorophenyl)methane.

Now, the effects obtained by the invention will be illustrated below:

First, the 2-arylnaphtho[1,8-bc]furan-5-ones of this invention can be easily prepared. That is, when a substituted or unsubstituted arylcarboxylic acid is reacted with 1,5-dihydroxynaphthalene while heating in the presence of a catalyst such as zinc chloride, a reaction, which is considered to be a multi stage reaction, proceeds in one reaction vessel to provide the object material. Furthermore, as shown in the examples described later, the material can be easily isolated and purified. Accordingly, the naphthoquinone can be produced at a very low cost as compared with conventional polymerization initiators which are produced through several stages of reaction.

The absorption maximum of the naphthofuranones of this invention at the longer wavelength side is in the region of 380 to 430 nm, which coincides well with the spectral energy distribution of a xenon light source or high-voltage mercury lamp usually used for image exposure. For this reason, the photopolymerizable composition containing the photopolymerization initiator of this invention is highly sensitive to these light sources as compared with photopolymerizable compositions containing conventional photopolymerization initiators. Since 2-arylnaphtho[1,8-bc]furan-5-ones have maximum light-sensitivity in the wavelength range which possesses the highest energy in the wavelength distribution of an actinic light, the naphthofuranones can efficiently absorb the energy of the actinic light and photodecompose, whereby photopolymerization takes place efficiently. Moreover, the printing plate utilizing the naphthofuranones of this invention shows very high resolving power and good reproducibility of dot images.

The photopolymerizable composition using the naphthofuranones of this invention exhibits very superior thermal stability. This is considered to be due to the fact that the naphthofuranones possess activity as a thermal polymerization inhibitor in the ground state and the photopolymerizable composition of this invention can provide products having long shelf life (the product keeps its original properties while stored).

Furthermore, the naphthofuranones of this invention show very remarkable synergistic effects with the amine series photopolymerization accelerators discussed above and, hence, possesses sensitivities which are difficult to obtain with conventional photopolymerization initiators. The synergistic effect is far superior with compositions obtained by combining conventional carbonyl compounds and amine series photopolymerization accelerators.

The detailed mechanism whereby the naphthofuranone of this invention initiates polymerization is not clear but based on the literature, it is believed that a radical having unpaired electrons is formed at the 2-position by hydrogen capture by the carbonyl group and isomerization to the benzenoid structure by light excitation as shown in formula (XVII) below.

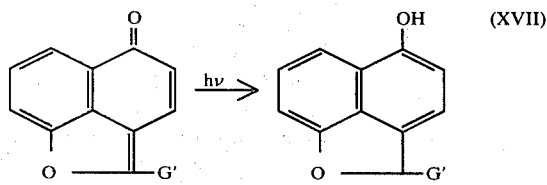

(XVII)

As shown in the examples described later, the naphthofuranones of the present invention are useful as a photooxidizing agents for oxidizable leuco dyes frequently used in the filed of free radical photography. Therefore, when a leuco dye is used together with the ethylenically unsaturated compound, it is possible to produce printing plates having a so-called print out aptitude wherein the imagewise exposed portions are simultaneously hardened and colored.

The production of the naphthofuranones will be explained in detail in Examples 1 to 19 and photopolymerizable compositions containing the naphthofuranones will be illustrated in Examples 20 to 184.

EXAMPLE 1

Preparation of Compound (II)-6

18.1 g of a zinc chloride powder was added to a fused mixture of 25.0 g of 3,5-dimethylbenzoic acid and 17.7 g of 1,5-dihydroxynaphthalene and stirred vigorously at 185° C. and reacted for 45 minutes. After the reaction was complete, the mixture was dissolved while hot in 200 ml of ethanol. Crude crystals recovered by crystallization at room temperature were boiled in ether together with activated carbon and then recrystallized to provide 4.5 g of yellow crystals of 2-(3,5-dimethylphenyl)naphtho[1,8-bc]furan-5-one having a melting point of 223.0° C. (yield 14.8%).

| Elemental Analysis for $C_{19}H_{14}O_2$: | | |
|---|---|---|
| | C | H |
| Calculated (%): | 83.20 | 5.15 |
| Found (%): | 82.95 | 5.12 |

Infrared Absorption Spectrum: 1635 cm$^{-1}$ ($\nu$C=O)
Nuclear Magnetic Resonance Spectrum: (CDCl$_3$) ($\delta$ value in ppm in CDCl$_3$ measured with respect to TMS (tetramethylsilane) used as an internal reference)
$\delta$: (ppm) 2.39 (s, 5.4H), 6.59 (d, 0.95H, J=10 Hz), 8.1–7.0 (m, 7.0H)

EXAMPLE 2

Preparation of Compound (II)-9

As in Example 1, 25 g of p-anisic acid was reacted with 17.5 g of 1,5-dihydroxynaphthalene in the presence of 18.0 g of zinc chloride for 40 minutes at 190° C. Crude crystals of the reaction mixture were crystallized from an ethanol solution and treated with activated carbon and then recrystallized from ethanol to provide 7.3 g (yield 30.7%) of orange plate crystals of 2-(4-methoxyphenyl)naphtho[1,8-bc]furan-5-oen (Compound (II)-9) having a melting point of 200.5° C.

| Elemental Analysis for $C_{18}H_{12}O_3$: | | |
|---|---|---|
| | C | H |
| Calculated (%): | 78.25 | 4.38 |
| Found (%): | 77.88 | 4.56 |

Infrared Absorption Spectrum: 1625 cm$^{-1}$ ($\nu$C=O)
Nuclear Magnetic Resonance Spectrum: (in dimethylsulfoxide-d$_6$) $\delta$: 3.85 (s, 2.8H), 8.1–7.0 (m, 9.0H)

EXAMPLE 3

Preparation of Compound (II)-5

18.1 g (0.133 mol) of powdery zinc oxide was added to 25.0 g (0.167 mol) of p-ethylbenzoic acid heated to fuse at 160° C. with stirring. After 5 minutes, 17.8 g (0.111 mol) of 1,5-dihydroxynaphthalene was added to the mixture over a 5 minute period followed by heating for 40 minutes. The oil bath was removed, 100 ml of ethanol was added to the mixture before the reaction mixture solidified and the reaction mixture was dissolved. After cooling the solution of the reaction mixture to room temperature, crude crystals were recovered by filtration. Recrystallization from ethanol provided 5.0 g (yield 16.4%) of the yellow-orange crystals of 2-(4-ethylphenyl)naphtho[1,8-bc]furan-5-one (Compound (II)-5) having a melting point of 185.5° C.

| Elemental Analysis for $C_{19}H_{14}O_2$: | | |
|---|---|---|
| | C | H |
| Calculated (%): | 83.20 | 5.15 |
| Found (%): | 80.91 | 5.12 |

In addition, recrystallization and vacuum sublimation were repeated. The calculated value did not coincide with the found value in the elemental analysis of the sample product but the m/e value of the parent ion in the mass spectrography and the existence ratio of isotopes were as shown below and the form of fragmentation was remarkable in de-carbon monoxide observed in other arylnaphthofuranones.

| Calculated Value: m/e = 274 | P + 1 = 20.82% |
| | P + 2 = 2.63% |
| Found Value: m/e = 274 | P + 1 = 20.50% |
| | P + 2 = 2.96% |

Furthermore, in the infrared absorption spectrum, the characteristic absorption of 1630 cm$^{-1}$ based on the carbonyl group was observed and further in the nuclear magnetic resonance spectrum (in dimethyl sulfoxide), the triplet of β-proton based on the ethyl group was observed at δ=1.28 as well as other spectra same as those presumed from the subjective material were recorded.

From these results, it was confirmed that the product was objective compound.

EXAMPLE 4

Preparation of Compound (II)-7

To a fused mixture of 42.8 g of o-anisic acid and 30 g of 1,5-dihydroxynaphthalene stirred at 150° C. was added 30.6 g of zinc oxide followed with heating for 50 minutes. The reaction mixture was poured into 1.5 liters of a saturated aqueous solution of sodium hydrogen carbonate and the mixture was stirred for 1 hour by means of an agitator. The residue was extracted with 900 ml of a 5% aqueous sodium hydroxide solution. The dried residue was extracted with benzene (by means of a Soxhlet's extractor) and the crude product obtained was recrystallized from ethanol to provide 4.8 g (yield 9.3%) of the yellow crystals of 2-(2-methoxyphenyl)-naphtho[1,8-bc]furan-5-one having a melting point of 144.5° C.

Elemental Analysis for $C_{18}H_{12}O_3$:

| | C | H |
|---|---|---|
| Calculated (%): | 78.25 | 4.38 |
| Found (%): | 78.45 | 4.39 |

Nuclear Magnetic Resonance Spectrum (CDCl$_3$): δ: 8.1–6.5 (m, 8.5H), 4.0 (s, 3.0H)

Infrared Absorption Spectrum: 1640 cm$^{-1}$ (νC=O)

EXAMPLE 5

Preparation of Compound (II)-10

In a reaction flask heated to 193° C. was fused 50.0 g of veratric acid and while stirring, 29.8 g of zinc chloride was added to the fused compound. After 5 minutes, 29.3 g of 1,5-dihydroxynaphthalene was added to the mixture and reacted for 45 minutes. The reaction mixture was dissolved in 1 liter of benzene. After boiling the solution with 6 g of activated carbon, the product was extracted twice with 500 ml of a 1% aqueous sodium hydroxide solution saturated with sodium chloride. The organic layer recovered was concentrated and the residue formed was recrystallized from ethanol to obtain 8.0 g (yield 14.4%) of the yellow-brown acicular crystals of 2-(3,4-dimethoxyphenyl)naphtho[1,8-bc]furan-5-one (Compound (II)-10).

Elemental Analysis for $C_{19}H_{14}O_4$:

| | C | H |
|---|---|---|
| Calculated (%): | 74.50 | 4.61 |
| Found (%): | 74.45 | 4.70 |

Infrared Absorption Spectrum: 1638 cm$^{-1}$ (νC=O)

Nuclear Magnetic Resonance Spectrum (CDCl$_3$): δ: 8.0–7.1 (m, 6.8H), 6.5 (d, 1.0H, J=10 Hz), 6.9 (d, 1.0H, J=10 Hz), 3.92 and 3.95 (doublet s, 6.0H)

EXAMPLES 6–15

As in Example 5, substituted benzoic acid was reacted with 1,5-dihydroxynaphthalene in the presence of zinc chloride. The product was isolated and then purified in the manner described in Example 5. The analytical values of the 2-arylnaphtho[1,8-bc]furan-5-ones are shown in Table 13.

TABLE 13

| Example | Compound No. | 2-Position Substituent | Crystal Form | Melting Point (°C) | Elemental Analysis (%) | IR (C = O) (cm$^{-1}$) | MS (m/e) parent peak* |
|---|---|---|---|---|---|---|---|
| 6 | II-2 | 2-methyl-phenyl | yellow needle-like crystal | 118 | C: 83.08 H: 4.90 (C: 83.06 H: 4.65)** | 1640 | 260 |
| 7 | II-3 | 3-methyl-phenyl | yellow needle-like crystal | 139 | C: 82.99 H: 4.59 (C: 83.06 H: 4.65) | 1640 | 260 |
| 8 | II-4 | 4-methyl-phenyl | yellow needle-like crystal | 149 | C: 83.28 H: 4.53 (C: 83.06 H: 4.65) | 1640 | 260 |
| 9 | II-8 | 3-methoxy-phenyl | yellow crystal | 194 | C: 78.39 H: 4.48 (C: 78.25 H: 4.38) | 1630 | 276 |
| 10 | II-11 | 2,4-dimethoxy-phenyl | yellow-orange crystal | 196 | C: 73.87 H: 5.00 (C: 74.50 H: 4.61) | 1635 | 306 |
| 11 | II-12 | 2-chloro-phenyl | light yellow-brown crystal | 181 | C: 72.62 H: 3.25 (C: 72.74 H: 3.23) | 1640 | 280 |
| 12 | II-13 | 3-chloro-phenyl | light yellow-brown crystal | 189 | C: 72.64 H: 3.31 (C: 72.74 H: 3.23) | 1640 | 280 |
| 13 | II-14 | 3-bromo-phenyl | light brown crystal | 190 | C: 62.53 H: 2.91 (C: 62.80 H: 2.79) | 1640 | 324 |
| 14 | II-15 | 1-naphthyl | yellow-brown crystal | 184 | C: 85.13 H: 4.14 (C: 85.12 H: 4.08) | 1635 | 296 |
| 15 | II-16 | 2-naphthyl | yellow-brown acicular | 208 | C: 85.10 H: 4.11 (C: 85.12 H: 4.08) | 1630 | 296 |

TABLE 13-continued

| Example | Compound No. | 2-Position Substituent | Crystal Form | Melting Point (°Co) | Elemental Analysis (%) | IR (C = O) (cm$^{-1}$) | MS (m/e) parent peak* |
|---|---|---|---|---|---|---|---|
| | | | crystal | | | | |

*:All values concided with the calculated values.
**:calculated values

EXAMPLES 16-19

By condensing p-isopropylbenzoic acid, p-n-butylbenzoic acid, p-tert-butylbenzoic acid, or o-ethoxybenzoic acid with 1,5-naphthalenediol in the presence of zinc chloride as in Example 5, Compounds (II)-17, (II)-18, (II)-19, and (II)-20 were obtained respectively. The properties of these compounds are shown below:

EXAMPLE 16

Compound (II)-17: 2-(4-Isopropylphenyl)naphtho[1,8-bc]furan-5-one
Yellow Crystal
Melting Point: 99° C.
Infrared Absorption Spectrum: 1635 cm$^{-1}$ ($\nu$C=O)
Nuclear Magnetic Resonance Spectrum (CDCl$_3$): $\delta$: 7.9–7.2 (m, 8.1H), 6.45 (d, 1.0H), 2.95 (m, 1.0H), 1.30 (d, 5.7H)

EXAMPLE 17:

Compound (II)-18: 2-(4-n-Butylphenyl)naphtho[1,8-bc]furan-5-one
Yellow Crystal
Melting Point: 74.0° C.
Infrared Absorption Spectrum: 1635 cm$^{-1}$ ($\nu$C=O)
Nuclear Magnetic Resonance Spectrum (CDCl$_3$): $\delta$: 8.1–7.2 (m, 8.0H), 6.5 (d, 0.9H), 2.65 (t, 1.9H), 1.9–0.8 (m, 7.4H)

EXAMPLE 18:

Compound (II)-19: 2-(4-tert-Butylphenyl)naphtho[1,8-bc]furan-5-one
Yellow Crystal
Melting Point: 127.5° C.
Infrared Absorption Spectrum: 1640 cm$^{-1}$ ($\nu$C=O)
Nuclear Magnetic Resonance Spectrum (CDCl$_3$): $\delta$: 8.2–7.2 (m, 8.5H), 6.6 (d, 1.0H), 1.38 (s, 9.0H)

EXAMPLE 19:

Compound (II)-20: 2-(2-Ethoxyphenyl)naphtho[1,8-bc]furan-5-one
Yellow Crystal
Melting Point: 122.0° C.
Infrared Absorption Spectrum: 1635 cm$^{-1}$ ($\nu$C=O)
Nuclear Magnetic Resonance Spectrum (CDCl$_3$): $\delta$: 8.2–6.9 (m, 8.3H), 6.6 (d, 1.0H), 4.2 (q, 2.0H), 1.5 (t, 3.0H)

EXAMPLES 20-64

(including comparison examples)

The examples show that various 2-aryl substituents of the naphthofuranone (b) can be used as photopolymerization initiators by themselves and also that when they are used together with specific amine series photopolymerization accelerator (c), they show the synergistic acceleration effect obtained. Hereinafter, "C" added after the number of example shows that the example is a comparison example.

The test method employed in the examples and comparison examples was as follows:

An aluminum plate 0.24 mm thick for lithographic printing plate grained by means of Carborundum (silicon carbide abrasive grain: trade name of Carborundum Co.) was coated with a solution of the photosensitive composition as shown below by means of a rotary coating machine and dried for 10 minutes at 80° C. Thus, a photosensitive material having a photosensitive layer of 8 $\mu$m dry thick was obtained.

A gray Scale (Fuji PS step-guide, made by the Fuji Photo Film Co., Ltd., an optical wedge having an adjacent optical density difference of 0.15 and a total of 15 stages. The first 0 stage having the lowest optical density of 0.06, and is based on the inherent absorption of the support) was closely placed on the photosensitive layer of the photosensitive material and after exposing for 15 seconds to a ultra-high voltage mercury lamp (ORC Jet Printer, 2 kw) at a distance of 55 cm, the photosensitive layer was developed with 1,1,1-trichloroethane for 60 seconds. Using this procedure, the unhardened portions of the photosensitive layer were dissolved away and only the hardened portions were left on the aluminum plate, and it could be easily developed with a lithographic printing lacquer. The minimum exposure amount necessary for light-hardening of the photosensitive layer is shown by the stage number of the Gray Scale at which a good hardened image is obtained. The stage number at which hardening occurs is, therefore, a measure of the sensitivity of the photosensitive material used. Based on this, the sensitivies of the photosensitive materials in the examples and comparison examples can be compared as shown in Table 14. (The mark "—" in the table means no image was obtained.) As the stage number increases, the sensitivity of the photosensitive material is higher and for the gray scale used, an increase of one stage means that the sensitivity is higher by a factor of $\sqrt{2}$. The numerical values in the column of sensitivity are the sensitivities measured as described above.

The photosensitive compositions were prepared as follows:

In 300 g of methyl ethyl ketone were dissolved 100 g of chlorinated polyethylene (chlorine content: about 69% by weight; viscosity: about 90 cps at 25° C. in a 40% by weight toluene solution) and 130 g of pentaerythritol trimethacrylate to form the polymerizable solution. A mixture of 0.16 mmol of the naphthofuranone of formula (II) shown in Table 14 and 0.16 mmol of the amine series photopolymerization accelerator as shown in Table 14, or 0.32 mmol of the naphthofuranone of formula (II) alone, or 0.32 mmol of the amine series photopolymerization accelerator alone, were added to 10 g of the polymerizable solution thus-obtained.

In addition, when Compound (II)-1 was used in the above-described compositions, the amount of Compound (II)-1 corresponded to 1.6% by weight based on the weight of the ethylenically unsaturated compound.

Also, the chlorinated polyethylene used was Superchlon 412,999 (trade name, made by Sanyo Kokusaku Pulp Co., Ltd.), its chlorination degree (chlorine content) was 70% by weight and its intrinsic viscosity in benzene at 30° C. was 0.140. The pentaerythritol trimethacrylate was a mixture of 3 parts by weight of pentaerythritol, 4 parts by weight of pentaerythritol dimethacrylate, 60 parts by weight of pentaerythritol trimethacrylate, and 33 parts by weight of pentaerythritol tetramethacrylate.

TABLE 14

| Example | Compound No. (b) | Amine Series Photopolymerization Accelerator (c) | Sensitivity (stage number) |
|---|---|---|---|
| 20 | II-1 | None | 5 |
| 21 | II-2 | None | 6 |
| 22 | II-3 | None | 6 |
| 23 | II-4 | None | 6 |
| 24 | II-5 | None | 6 |
| 25 | II-6 | None | 6 |
| 26 | II-7 | None | 6 |
| 27 | II-8 | None | 5 |
| 28 | II-9 | None | 5 |
| 29 | II-10 | None | 4 |
| 30 | II-11 | None | 4 |
| 31 | II-12 | None | 5 |
| 32 | II-13 | None | 5 |
| 33 | II-14 | None | 5 |
| 34 | II-15 | None | 1 |
| 35 | II-16 | None | 4 |
| 36 | II-17 | None | 5 |
| 37 | II-18 | None | 5 |
| 38 | II-19 | None | 5 |
| 39 | II-20 | None | 5 |
| 40 | II-1 | IV-5 | 11 |
| 41 | II-2 | IV-5 | 11 |
| 42 | II-3 | IV-5 | 11 |
| 43 | II-4 | IV-5 | 10 |
| 44 | II-5 | IV-5 | 10 |
| 45 | II-6 | IV-5 | 11 |
| 46 | II-7 | IV-5 | 10 |
| 47 | II-8 | IV-5 | 11 |
| 48 | II-9 | IV-5 | 9 |
| 49 | II-10 | IV-5 | 9 |
| 50 | II-11 | IV-5 | 9 |
| 51 | II-12 | IV-5 | 12 |
| 52 | II-13 | IV-5 | 12 |
| 53 | II-14 | IV-5 | 11 |
| 54 | II-15 | IV-5 | 8 |
| 55 | II-16 | IV-5 | 10 |
| 56 | II-18 | IV-5 | 11 |
| 57 | II-20 | IV-5 | 10 |
| 58 | II-3 | III-1 | 12 |
| 59 | II-7 | III-1 | 11 |
| 60 | II-10 | III-1 | 9 |
| 61 | II-12 | III-1 | 11 |
| 62 | II-16 | III-1 | 11 |
| 63C | None | IV-5 | 2 |
| 64C | None | III-1 | — |

From the results shown in Table 14, it it clear that the naphthofuranone is useful as a photopolymerization initiator by itself (Examples 20–39) and also the use of triethanolamine (III)-1 (Examples 58–62) or Michler's ketone (IV)-5 (Examples 40–57) together with the naphthofuranone shows a synergistic photopolymerization acceleration effect as compared with the cases of using them individually at the same corresponding amount.

EXAMPLES 65–158

(including comparison examples)

The following examples show the effect when various kinds of the amine series initiators or auxiliary initiators (c) were added to the specific naphthofuranones (b). The test method was same as in Example 20 and the results are shown in Table 15.

TABLE 15

| Example | Compound No. (b) | Amine Series Photopolymerization Accelerator (c) | Sensitivity (stage number) |
|---|---|---|---|
| 20 | II-1 | None | 5 |
| 65 | II-1 | III-1 | 14 |
| 66 | II-1 | III-2 | 13 |
| 67 | II-1 | III-7 | 12 |
| 68 | II-1 | III-5 | 10 |
| 69C | None | III-1 | — |
| 70C | None | III-2 | — |
| 71C | None | III-7 | — |
| 72C | None | III-5 | — |
| 73 | II-1 | IV-1 | 10 |
| 74 | II-1 | IV-2 | 9 |
| 75 | II-1 | IV-3 | 9 |
| 76 | II-1 | IV-4 | 10 |
| 77 | II-1 | IV-6 | 8 |
| 78 | II-1 | IV-8 | 10 |
| 79C–84C | None | Each of IV-1, IV-2, IV-3, IV-4, IV-6, IV-8 | 0–2 |
| 85 | II-1 | V-2 | 10 |
| 86 | II-1 | V-3 | 9 |
| 87 | II-1 | V-4 | 9 |
| 88 | II-1 | V-6 | 9 |
| 89 | II-1 | V-7 | 9 |
| 90 | II-1 | V-8 | 9 |
| 91 | II-1 | V-15 | 11 |
| 92 | II-1 | V-16 | 10 |
| 93 | II-1 | V-21 | 10 |
| 94C–102C | None | each of V-2, V-3, V-4, V-6, V-7, V-8, V-15, V-16, V-21 | 0–1 |
| 103 | II-1 | VI-1 | 9 |
| 104 | II-1 | VI-3 | 8 |
| 105C and 106C | None | each of VI-1, VI-3 | 0–1 |
| 107 | II-1 | VI-4 | 9 |
| 108 | II-1 | VII-5 | 9 |
| 109 | II-1 | VII-15 | 9 |
| 110 | II-1 | VII-27 | 9 |
| 111 | II-1 | VII-1 | 8 |
| 112 | II-1 | VII-3 | 8 |
| 113 | II-1 | VII-11 | 8 |
| 114C–120C | None | each of VII-4, VII-5, VII-15, VII-27, VII-1, VII-3, VII-11 | 0–1 |
| 121 | II-1 | VIII-3 | 9 |
| 122 | II-1 | VIII-7 | 9 |
| 123 | II-1 | VIII-1 | 8 |
| 124 | II-1 | VIII-5 | 8 |
| 125 | II-1 | VIII-12 | 8 |
| 126C–130C | None | Each of VIII-3, VIII-7, VIII-1, VIII-5, VIII-12 | 0–2 |
| 131 | II-1 | IX-8 | 11 |
| 132 | II-1 | IX-14 | 11 |
| 133 | II-1 | IX-5 | 10 |
| 134 | II-1 | IX-11 | 10 |
| 135 | II-1 | IX-3 | 9 |
| 136 | II-1 | IX-4 | 9 |
| 137C–142C | None | each of IX-8, IX-14, IX-5, IX-11, IX-3, IX-4 | 2–3 |
| 143 | II-1 | X-2 | 10 |
| 144 | II-1 | X-1 | 9 |
| 145 | II-1 | X-4 | 9 |
| 146C–148C | None | each of X-2, X-1, X-4 | 0–1 |
| 149 | II-1 | XI-1 | 9 |
| 150 | II-1 | XI-2 | 9 |
| 151 | II-1 | XI-3 | 9 |
| 152C | None | X-1 | 1 |
| 153C | None | X-2 | 2 |
| 154C | None | X-3 | 1 |
| 155 | II-1 | XII-1 | 9 |
| 156 | II-1 | XII-2 | 9 |
| 157C | None | XII-1 | — |

TABLE 15-continued

| Example | Compound No. (b) | Amine Series Photopolymerization Accelerator (c) | Sensitivity (stage number) |
|---|---|---|---|
| 158C | None | XII-2 | — |

From the results shown in Table 15, it is clear that the photosensitive compositions containing Compound (II)-1 (the novel photopolymerization initiator selected as a typical example of the naphthofuranones of the present invention) together with various amine series accelerators exhibits higher hardening sensitivity than photopolymerizable compositions (comparison examples) containing a corresponding amount of Compound (II)-1 individually (Example 20) or a corresponding amount of the amine series photopolymerization accelerator individually. In addition, the sensitivity in the case of using the amine series photopolymerization accelerator individually in the comparison experiment is shown by the range obtained for the compound having each general formula. The compounds (c) having the same general formula showed similar individual sensitivities.

EXAMPLES 159–167

The following examples show the limits of the mixing ratio of the 2-component initiator system can be changed without losing the synergistic effect. The photopolymerizable compositions used in the tests were prepared by adding a mixture of Compounds (II)-1 and (V)-2 to 10 g of a photopolymerizable composition obtained by dissolving 100 g of chlorinated polyethylene (chlorine content: about 69% by weight; viscosity at 25° C. in a 40% by weight toluene solution: about 90 cps) and 130 g of pentaerythritol trimethacrylate in 300 g of methyl ketone while changing the mixing ratio of Compound (II)-1 to Compound (V)-2 as shown in Table 16. The reuslts are shown in Table 16.

TABLE 16

| | Two Components Mol Ratio and Sensitivity | | |
|---|---|---|---|
| Example | Compound (II)-1 (weight ratio to monomer) | Compound (V)-2 (mol ratio of (II)-1/(V)-2) | Sensitivity |
| 159 | 2.45 mg (0.1%) | None | 1 |
| 160 | 24.5 mg (1.0%) | None | 5 |
| 161 | 73.5 mg (3.0%) | None | 7 |
| 162 | 122.5 mg (5.0%) | None | 7 |
| 163 | 0.16 mmol (40 mg) | None | 5 |
| 164 | 0.16 mmol (40 mg) | 0.008 mmol (1.6 mg) (1/20) | 6 |
| 165 | 0.16 mmol | 0.032 mmol (6.5 mg) (1/5) | 8 |
| 166 | 0.16 mmol | 0.16 mmol (32.5 mg) (1/1) | 10 |
| 167 | 0.16 mmol | 0.80 mmol (162 mg) (5/1) | 10 |

EXAMPLES 176 AND COMPARISON EXAMPLES 168–175

In the following examples and comparison examples, the synergistic effect of the triethanolamine selected as a typical example of the amine series photopolymerization initiators for different carbonyl compounds is compared. The test method and the amount of triethanolamine and carbonyl compound were the same as for the amine and naphthofuranone in Example 20. The reuslts show the difference between the gray scale stage numbers for the case using the triethanolamine and the case of not using the amine.

TABLE 17

| | Synergistic Acceleration Effect of Triethanolamine for Various Carbonyl Compounds | |
|---|---|---|
| Example | Carbonyl Compound | Synergistic Effect (difference in stage numbers of gray scale with and without triethanolamine) |
| 168C | benzophenone | +1 |
| 169C | benzil | +1 |
| 170C | fluorenone | +1 |
| 171C | 9,10-phenanthraquinone | +1 |
| 172C | 1-methyl-2-benzoyl-methylene-β-naptho-thiazoline | +0 |
| 173C | 3-ethyl-2-benzoyl-methylene-α-naphtho-thiazoline | +0 |
| 174C | 9,10-anthraquinone | +1 |
| 175C | xanthone | +1 |
| 176 | Compound (II)-1 | +7 |

From the results shown in the above table, it is clear that Compound (II)-1 (Example 176) which is the novel photopolymerization initiator shows a remarkable synergistic photopolymerization acceleration effect for the amine compound as compared with conventional carbonyl group-containing photopolymerization initiators (Comparison Examples 168–175).

EXAMPLES 177–183

(including comparison examples)

An aluminum plate (an aluminum alloy consisting of 96.9–97.4% by weight aluminum, 1.0–1.5% by weight manganese, and about 1.6% by weight other minor components) for lithographic printing was immersed in an aqueous solution of 5% trisodium phosphate at 70° C. for 5 minutes to clean the oils attached to the surface thereof during rolling. By the immersion treatment, some etching of the surface occurred which increased the plate's water-holding capacity. The plate was washed with water, immersed in an aqueous solution of 70% nitric acid, washed with water, grained by carborundum, and then washed with water.

The aluminum plate was anodically oxidized in a 20% sulfuric acid solution for 2 minutes at a current density of 3 A/dm$^2$ at 50° C. followed by water washing and drying. The plate was then immersed in an aqueous 1% phosphoric acid solution of 70° C. for 2 minutes, washed with water and coated with an aqueous solution of 1.0% polyvinylpyrrolidone K-30 (made by Tokyo Kasei Kogyo Co.) by means of a whirler rotary coating machine followed by drying.

On the other hand, a solution of photosensitive composition was prepared by dissolving the composition shown below in a mixture of 100 ml of methyl ethyl ketone and 20 ml of dimethylformamide.

| | |
|---|---|
| Chlorianted Polyethylene, Superchlon CPE-907 LTA* (trade name, made by Sanyo Kokusaku Pulp Co., Ltd.) | 10 g |
| Pentaerythritol trimethacrylate | 10 g |
| Photopolymerization initiator (and/or photopolymerization accelerator) | shown in Table 18 |
| Hydroquinone | 0.1 g |

-continued

| | |
|---|---|
| Copper Phthalocyanine Pigment | 0.2 g |

*:Superchlon CPS-907 LTA is a chlorinated polyethylene having a chlorine content above 69% by weight and a viscosity in 40% toluene solution at 25° C. of about 90 cps.

The solution was coated on the above-mentioned aluminum plate surface treated and undercoated with the hydrophilic polymer, by means of a rotary coating machine and dried for 2 minutes at 120° C. The dry thickness of the photosensitive layer was 4 μm. Then, a polyethylene terephthalate film of 16 μm thick was laminated on the photosensitive layer by pressing at room temperature.

The photopolymerization initiators and the property of the photosensitive plates thus-prepared are shown in Table 18.

TABLE 18

| Example | Photopolymerization Initiator | Amount (g) | Final Stage Number of Step Wedge |
|---|---|---|---|
| 177C | 2-methylanthraquinone | 0.2 | 2 |
| 178C | 2-tert-butylanthraquinone | 0.2 | 2 |
| 179 | Compound (II)-1 alone | 0.2 | 4 |
| 180 | Compound (II)-1 | 0.2 | |
| | Michler's ketone | 0.2 | 12 |
| 181 | Compound (II)-1 | 0.2 | |
| | triethanolamine | 0.1 | 12 |
| 182C | Michler's ketone | 0.2 | — |
| 183C | triethanolamine | 0.1 | — |

In each of the photosensitive lithographic printing materials in above-mentioned three examples and four comparison examples, a negative image to be printed and a step wedge having 0.15 stage difference were placed closely on the polyethylene terephthalate film on the photosensitive layer and the imagewise exposure was performed for 20 seconds using a PS Light S Type (a metal halide lamp of 2 kw, made by the Fuji Photo Film Co., Ltd.) at a distance of 1 meter. Then, the polyethylene terephthalate film was stripped off immediately, whereby light-hardened positive images were formed on the aluminum plate and the unhardened portions (unexposed portions) were removed together with the polyethylene terephthalate film for Examples 179–181 and Comparison Examples 177C and 187C. For Comparison Examples 182C and 183C, on the other hand, the light-hardened positive images were not left on the aluminum plate. Then, to complete the hardening of the positive images formed, the printing plates obtained were placed under a mercury lamp of 4 kw at a distance of 10 cm, coveyed at a speed of 30 mm/sec. The stage number corresponding to the minimum exposure amount of step wedge left on the aluminum plate is shown as the sensitivity.

The lithographic printing plate prepared in each of Examples 179–181 and Comparison Examples 177C and 178C was then subjected to a gumming treatment with an aqueous gum arabic solution (a solution of 5 g of gum arabic in 100 ml of water), and mounted on a printing machine (Davidson Dualis 700), and the offset printing was run under same conditions. The results are shown in the following table.

TABLE 19

| Example | (A) | (B) | (C) | (D) | (E) |
|---|---|---|---|---|---|
| Examples 179, 180 and 181 | O | O | O | O | O |
| Comparison Examples | | | | | |
| 177C and 178C | × | Δ | Δ | Δ | Δ |

(A): Stain formation,
(B): Printability,
(C): Ink-reception,
(D): Time stability, and
(E): Total evaluation.
"Printability" is the number of usable copies obtained when printed under same conditions.
O: 150,000 or more copies
Δ: 30,000 or more copies
"Ink-reception" and "Stain formation" are the appearance of a printed material after printing a definite number of copies.
O: Practically good (no problem)
Δ: A little bad
×: No practical use
"Time stability" is the stability of a photosensitive lithographic printing plate material when it is placed under a yellow safe light (25° C.) for a definite period of time.
O: Stable after passing 6 months
Δ: Substantially stable until 5 weeks From the above tests, it was confirmed that the photosensitive lithographic printing plate materials prepared using Compound (II)-1 of this invention individually as a photopolymerization initiator had a sensitivity about twice as high as that of photosensitive lithographic printing plate materials prepared using conventional photopolymerization initiators, that the use of Michler's ketone or triethanolamine which was the amine series photopolymerization accelerator (or auxiliary photopolymerization initiator) together with Compound (II)-1 increased the sensitivity about 16 times, and that the photosensitive lithographic printing plate materials of this invention has excellent time stability and printability.

EXAMPLE 184

A solution of photosensitive composition was prepared by dissolving the following composition in a mixture of 100 ml of acetone and 1 ml of triethylene glycol.

| | |
|---|---|
| Cellulose Acetate Butyrate | 10.0 g |
| Compound (II)-1 | 1.0 g |
| Tris(4-diethylaminophenyl)methane | 0.4 g |
| p-Toluenesulfonic Acid | 0.4 g |

The photosensitive composition solution was coated on a polyethylene terephthalate film of 100 μm thick so that the dry thickness of the photosensitive layer became 10 μm, and dried to provide a photosensitive material. When the photosensitive material was exposed through a positive original image to a tungsten lamp of 1 kw in a slide projector at a distance of 50 cm form the front end of the projection lens of the slide projector (lens f=130 mm, f/3.5) for 10 seconds using a water filter layer of 20 mm between them for shielding heat, a positive colored image was obtained.

For comparison, a photosensitive material was prepared by the same manner as above except that Compound (II)-1 was not used and the photosensitive material was image exposed under the same conditions as above. A colored image was not obtained.

While the invention has been described in detail and with reference to specific embodiments thereof, it will be apparent to one skilled in the art that various changes and modifications can be made therein without departing from the spirit and scope thereof.

What is claimed is:

1. A 2-arylnaphtho[1,8-bc]furan-5-one represented by the general formula (I):

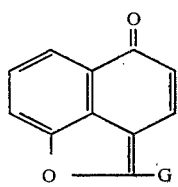

wherein G represents a substituted phenyl group, an unsubstituted or substituted 1-naphthyl group and an unsubstituted or substituted 2-naphthyl group, with the substituents being selected from the group consisting of a straight chain or branched chain alkyl group having 1 to 5 carbon atoms, a straight chain or branched chain alkoxy group having 1 to 3 carbon atoms and a chlorine atom.

2. The 2-arylnaphtho[1,8-bc]furan-5-one as claimed in claim 1, wherein G is a phenyl group substituted with one or two of a methyl group, an ethyl group, a n-propyl group, a n-butyl group, an isopropyl group, an isobutyl group, a sec-butyl group, a tert-butyl group, a methoxy group, an ethoxy group, or a chlorine atom; or G is a 1-naphthyl group or a 2-naphthyl group.

3. A 2-arylnaphtho[1,8-bc]furan-5-one represented by the general formula (I):

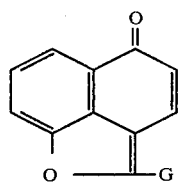

wherein G represents a substituted phenyl group, an unsubstituted or substituted 1-naphthyl group and an unsubstituted or substituted 2-naphthyl group, with the substituents being selected from the group consisting of a straight chain or branched chain alkyl group having 1 to 5 carbon atoms and a straight chain or branched chain alkoxy group having 1 to 3 carbon atoms.

4. The 2-arylnaphtho[1,8-bc]furan-5-one as claimed in claim 3, wherein G is a phenyl group substituted with one or two of a methyl group, an ethyl group, a n-propyl group, a n-butyl group, an isopropyl group, an isobutyl group, a sec-butyl group, a tert-butyl group, a methoxy group or an ethoxy group; or G is a 1-naphthyl group or a 2-naphthyl group.

* * * * *